(12) United States Patent
Cohen et al.

(10) Patent No.: US 9,744,044 B2
(45) Date of Patent: *Aug. 29, 2017

(54) UNICONDYLAR TIBIAL KNEE IMPLANT

(71) Applicant: Mako Surgical Corp., Fort Lauderdale, FL (US)

(72) Inventors: Robert Craig Cohen, Bernardsville, NJ (US); Philip Harris Frank, Maplewood, NJ (US)

(73) Assignee: Mako Surgical Corp., Fort Lauderdale, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/212,051

(22) Filed: Mar. 14, 2014

(65) Prior Publication Data

US 2014/0277548 A1 Sep. 18, 2014

Related U.S. Application Data

(60) Provisional application No. 61/794,339, filed on Mar. 15, 2013.

(51) Int. Cl.
*A61F 2/36* (2006.01)
*A61F 2/30* (2006.01)
(Continued)

(52) U.S. Cl.
CPC ...... *A61F 2/30771* (2013.01); *A61B 17/1675* (2013.01); *A61F 2/38* (2013.01); *A61F 2/389* (2013.01); *A61F 2/3859* (2013.01); *A61F 2/30744* (2013.01); *A61F 2002/30062* (2013.01); *A61F 2002/30884* (2013.01); *A61F 2002/30967* (2013.01); *A61F 2002/3895* (2013.01)

(58) Field of Classification Search
CPC .. A61F 2002/30884; A61F 2002/30896; A61F 2/389
USPC ................... 623/20.3, 20.32, 19.13
See application file for complete search history.

(56) References Cited

U.S. PATENT DOCUMENTS 3,715,763 A 2/1973 Link
3,774,244 A 11/1973 Walker
(Continued)

FOREIGN PATENT DOCUMENTS

CN 100502808 C 6/2009
EP 0611559 A1 8/1994
WO 2011110865 A2 9/2011

OTHER PUBLICATIONS

Berger et. al. Results of Unicompartmental Knee Arthroplasty at a Minimum of Ten Years of Follow. Journal of Bone and Joint Surgery; May 2005; 87, 5; Proquest Central, p. 999.
(Continued)

*Primary Examiner* — Alvin Stewart
(74) *Attorney, Agent, or Firm* — Lerner, David, Littenberg, Krumholz & Mentlik, LLP

(57) ABSTRACT

An implant providing for both short and long term stability and fixation is disclosed. The implant includes a plurality of projections extending from a bone contacting surface, and a porous material covering at least portions of the surface and projections. The orientation of the projections and the porous material provide for the stability and fixation. Methods of forming and utilizing the implant are also disclosed.

24 Claims, 32 Drawing Sheets

(51) Int. Cl.
*A61F 2/38* (2006.01)
*A61B 17/16* (2006.01)

(56) References Cited

U.S. PATENT DOCUMENTS

| | | | |
|---|---|---|---|
| 3,824,630 A | 7/1974 | Johnston | |
| 3,852,830 A | 12/1974 | Marmor | |
| 3,958,278 A | 5/1976 | Lee et al. | |
| 4,001,896 A | 1/1977 | Arkangel | |
| 4,034,418 A | 7/1977 | Jackson et al. | |
| 4,085,466 A | 4/1978 | Goodfellow et al. | |
| 4,224,696 A | 9/1980 | Murray et al. | |
| 4,309,778 A | 1/1982 | Buechel et al. | |
| 4,711,639 A | 12/1987 | Grundei | |
| 4,719,908 A | 1/1988 | Averill et al. | |
| 4,743,261 A | 5/1988 | Epinette | |
| 4,795,468 A * | 1/1989 | Hodorek et al. | 623/20.28 |
| 4,935,023 A | 6/1990 | Whiteside et al. | |
| 4,944,757 A * | 7/1990 | Martinez et al. | 623/20.15 |
| 4,978,357 A | 12/1990 | Goymann et al. | |
| 5,037,439 A | 8/1991 | Albrektsson et al. | |
| 5,080,673 A | 1/1992 | Burkhead et al. | |
| 5,080,675 A | 1/1992 | Lawes et al. | |
| 5,152,797 A * | 10/1992 | Luckman et al. | 623/20.16 |
| 5,171,244 A | 12/1992 | Caspari et al. | |
| 5,171,276 A * | 12/1992 | Caspari et al. | 623/16.11 |
| 5,201,881 A | 4/1993 | Evans | |
| 5,203,807 A | 4/1993 | Evans et al. | |
| 5,226,915 A | 7/1993 | Bertin | |
| 5,246,459 A | 9/1993 | Elias | |
| 5,258,032 A | 11/1993 | Bertin | |
| 5,271,737 A * | 12/1993 | Baldwin et al. | 623/20.34 |
| 5,282,866 A | 2/1994 | Cohen et al. | |
| 5,312,411 A | 5/1994 | Steele et al. | |
| 5,314,487 A * | 5/1994 | Schryver et al. | 623/22.37 |
| 5,330,533 A | 7/1994 | Walker et al. | |
| 5,336,266 A | 8/1994 | Caspari et al. | |
| 5,413,604 A | 5/1995 | Hodge | |
| 5,480,444 A | 1/1996 | Incavo et al. | |
| 5,507,820 A | 4/1996 | Pappas | |
| 5,514,183 A | 5/1996 | Epstein et al. | |
| 5,520,695 A | 5/1996 | Luckman | |
| 5,534,027 A | 7/1996 | Hodorek | |
| 5,609,645 A | 3/1997 | Vinciguerra | |
| 5,658,341 A | 8/1997 | Delfosse | |
| 5,716,361 A | 2/1998 | Masini | |
| 5,755,801 A | 5/1998 | Walker et al. | |
| 5,782,925 A | 7/1998 | Collazo et al. | |
| 5,824,103 A | 10/1998 | Williams | |
| 5,871,542 A | 2/1999 | Goodfellow et al. | |
| 5,879,389 A | 3/1999 | Koshino | |
| 5,906,643 A | 5/1999 | Walker | |
| 5,911,758 A | 6/1999 | Oehy et al. | |
| 5,989,261 A | 11/1999 | Walker et al. | |
| 6,059,831 A | 5/2000 | Braslow et al. | |
| 6,068,658 A | 5/2000 | Insall et al. | |
| 6,102,951 A * | 8/2000 | Sutter et al. | 623/18.11 |
| 6,102,954 A | 8/2000 | Albrektsson et al. | |
| 6,132,468 A | 10/2000 | Mansmann | |
| 6,152,962 A * | 11/2000 | DeCarlo, Jr. | 623/22.34 |
| 6,179,876 B1 * | 1/2001 | Stamper et al. | 623/18.11 |
| 6,224,632 B1 * | 5/2001 | Pappas et al. | 623/20.34 |
| 6,264,697 B1 | 7/2001 | Walker | |
| 6,342,075 B1 | 1/2002 | MacArthur | |
| 6,344,059 B1 | 2/2002 | Krakovits et al. | |
| 6,379,388 B1 * | 4/2002 | Ensign | A61F 2/389 |
| | | | 623/20.21 |
| 6,475,241 B2 | 11/2002 | Pappas | |
| 6,491,726 B2 | 12/2002 | Pappas | |
| 6,494,914 B2 | 12/2002 | Brown et al. | |
| 6,506,216 B1 * | 1/2003 | McCue | A61F 2/389 |
| | | | 623/20.14 |
| 6,554,838 B2 | 4/2003 | McGovern et al. | |
| 6,554,866 B1 | 4/2003 | Aicher et al. | |
| 6,558,426 B1 | 5/2003 | Masini | |
| 6,616,696 B1 | 9/2003 | Merchant | |
| 6,620,198 B2 | 9/2003 | Burstein et al. | |
| 6,749,638 B1 | 6/2004 | Saladino | |
| 6,770,097 B2 | 8/2004 | Leclercq | |
| 6,797,006 B2 | 9/2004 | Hodorek | |
| 6,840,960 B2 | 1/2005 | Bubb | |
| 6,890,358 B2 * | 5/2005 | Ball et al. | 623/21.13 |
| 6,916,324 B2 | 7/2005 | Sanford et al. | |
| 6,946,001 B2 | 9/2005 | Sanford et al. | |
| 6,966,928 B2 * | 11/2005 | Fell et al. | 623/14.12 |
| 6,969,393 B2 | 11/2005 | Pinczewski et al. | |
| 7,048,741 B2 | 5/2006 | Swanson | |
| 7,083,652 B2 * | 8/2006 | McCue et al. | 623/20.34 |
| 7,094,241 B2 | 8/2006 | Hodorek et al. | |
| 7,105,027 B2 * | 9/2006 | Lipman et al. | 623/20.29 |
| 7,150,761 B2 | 12/2006 | Justin et al. | |
| 7,258,701 B2 | 8/2007 | Aram et al. | |
| 7,294,149 B2 | 11/2007 | Hozack et al. | |
| 7,357,817 B2 | 4/2008 | D'Alessio, II | |
| 7,465,320 B1 | 12/2008 | Kito et al. | |
| 7,524,334 B2 * | 4/2009 | Haidukewych | 623/20.32 |
| 7,537,664 B2 | 5/2009 | O'Neill et al. | |
| 7,544,210 B2 | 6/2009 | Schaefer et al. | |
| 7,572,293 B2 | 8/2009 | Rhodes et al. | |
| 7,578,850 B2 | 8/2009 | Kuczynski et al. | |
| 7,608,079 B1 | 10/2009 | Blackwell et al. | |
| 7,678,115 B2 | 3/2010 | D'Alessio, II et al. | |
| 7,708,741 B1 | 5/2010 | Bonutti | |
| 7,753,960 B2 | 7/2010 | Cipolletti et al. | |
| 7,842,092 B2 | 11/2010 | Otto et al. | |
| 7,850,698 B2 | 12/2010 | Straszheim-Morley et al. | |
| 7,862,619 B2 | 1/2011 | Clark | |
| 7,896,923 B2 | 3/2011 | Blackwell et al. | |
| 7,896,924 B1 | 3/2011 | Servidio | |
| 7,981,159 B2 | 7/2011 | Williams et al. | |
| 7,998,205 B2 * | 8/2011 | Hagen et al. | 623/14.12 |
| 8,080,063 B2 | 12/2011 | Ferrand et al. | |
| 8,083,803 B2 | 12/2011 | Albertorio et al. | |
| 8,100,981 B2 * | 1/2012 | Clark | A61F 2/389 |
| | | | 623/20.3 |
| 8,114,165 B2 | 2/2012 | Rhodes et al. | |
| 8,137,407 B2 | 3/2012 | Todd et al. | |
| 8,142,510 B2 | 3/2012 | Lee et al. | |
| 8,147,558 B2 * | 4/2012 | Lee | A61F 2/3868 |
| | | | 623/20.3 |
| 8,157,868 B2 | 4/2012 | Walker et al. | |
| 8,163,027 B2 | 4/2012 | Rhodes et al. | |
| 8,187,336 B2 | 5/2012 | Jamali | |
| 8,192,498 B2 | 6/2012 | Wagner et al. | |
| 8,202,323 B2 | 6/2012 | Wyss et al. | |
| 8,211,041 B2 | 7/2012 | Fisher et al. | |
| 8,226,727 B2 * | 7/2012 | Clark et al. | 623/20.36 |
| 8,234,097 B2 * | 7/2012 | Steines et al. | 703/1 |
| 8,236,061 B2 | 8/2012 | Heldreth et al. | |
| 8,273,131 B2 | 9/2012 | Metzger et al. | |
| 8,328,874 B2 | 12/2012 | Lee | |
| 8,337,564 B2 | 12/2012 | Shah et al. | |
| 8,361,147 B2 * | 1/2013 | Shterling et al. | 623/14.12 |
| 8,366,783 B2 | 2/2013 | Samuelson et al. | |
| 8,382,848 B2 | 2/2013 | Ries et al. | |
| 8,403,993 B2 | 3/2013 | Aram et al. | |
| 8,409,293 B1 | 4/2013 | Howard et al. | |
| 8,470,047 B2 | 6/2013 | Hazebrouck et al. | |
| 8,470,048 B2 | 6/2013 | Wolfson et al. | |
| 8,500,816 B2 | 8/2013 | Dees, Jr. et al. | |
| 8,506,571 B2 | 8/2013 | Chana et al. | |
| 8,540,778 B2 * | 9/2013 | Rhodes et al. | 623/20.34 |
| 8,632,600 B2 * | 1/2014 | Zannis et al. | 623/20.17 |
| 8,758,445 B2 | 6/2014 | Gupta et al. | |
| 8,945,229 B2 * | 2/2015 | Lappin | 623/19.13 |
| 2002/0095214 A1 * | 7/2002 | Hyde, Jr. | 623/18.12 |
| 2002/0173855 A1 | 11/2002 | Mansmann | |
| 2003/0014122 A1 * | 1/2003 | Whiteside | 623/20.32 |
| 2003/0060884 A1 * | 3/2003 | Fell et al. | 623/14.12 |
| 2003/0100953 A1 * | 5/2003 | Rosa et al. | 623/20.3 |
| 2003/0114933 A1 * | 6/2003 | Bouttens et al. | 623/19.13 |
| 2004/0006393 A1 | 1/2004 | Burkinshaw | |
| 2004/0153087 A1 | 8/2004 | Sanford et al. | |
| 2004/0167630 A1 * | 8/2004 | Rolston | 623/20.14 |

(56) References Cited

U.S. PATENT DOCUMENTS

| | | |
|---|---|---|
| 2004/0193280 A1* | 9/2004 | Webster et al. ............ 623/20.33 |
| 2005/0021145 A1* | 1/2005 | de Villiers ............ A61F 2/4425 623/17.14 |
| 2005/0033424 A1* | 2/2005 | Fell ............... 623/14.12 |
| 2005/0065611 A1* | 3/2005 | Huppert ............... A61F 2/4425 623/17.15 |
| 2005/0112397 A1* | 5/2005 | Rolfe et al. ................ 428/593 |
| 2005/0165491 A1 | 7/2005 | Diaz |
| 2005/0169893 A1* | 8/2005 | Koblish et al. ............ 424/93.7 |
| 2005/0171604 A1 | 8/2005 | Michalow |
| 2005/0192674 A1 | 9/2005 | Ferree |
| 2005/0203631 A1 | 9/2005 | Daniels et al. |
| 2005/0261775 A1* | 11/2005 | Baum et al. ............. 623/19.12 |
| 2006/0015113 A1 | 1/2006 | Masini |
| 2006/0064169 A1 | 3/2006 | Ferree |
| 2006/0129246 A1 | 6/2006 | Steffensmeier |
| 2006/0147332 A1 | 7/2006 | Jones et al. |
| 2006/0149387 A1* | 7/2006 | Smith ............... A61F 2/4081 623/19.11 |
| 2006/0155383 A1* | 7/2006 | Smith et al. ............. 623/23.51 |
| 2006/0157543 A1* | 7/2006 | Abkowitz ........... A61F 2/30767 228/233.2 |
| 2006/0178749 A1 | 8/2006 | Pendleton et al. |
| 2006/0190086 A1 | 8/2006 | Clemow et al. |
| 2006/0195196 A1 | 8/2006 | Pendleton et al. |
| 2006/0200248 A1* | 9/2006 | Beguin ............... A61F 2/4081 623/19.11 |
| 2006/0217734 A1 | 9/2006 | Sanford et al. |
| 2006/0235537 A1* | 10/2006 | Kuczynski et al. ......... 623/20.3 |
| 2006/0235541 A1 | 10/2006 | Hodorek |
| 2006/0287733 A1 | 12/2006 | Bonutti |
| 2007/0055269 A1 | 3/2007 | Iannarone et al. |
| 2007/0067032 A1* | 3/2007 | Felt et al. ............. 623/14.12 |
| 2007/0083266 A1* | 4/2007 | Lang ............. 623/17.11 |
| 2007/0100460 A1 | 5/2007 | Rhodes |
| 2007/0100461 A1 | 5/2007 | Incavo et al. |
| 2007/0142914 A1 | 6/2007 | Jones et al. |
| 2007/0173946 A1* | 7/2007 | Bonutti ............. 623/20.14 |
| 2007/0233269 A1* | 10/2007 | Steines et al. ............ 623/20.21 |
| 2007/0244564 A1* | 10/2007 | Ferrand ............. A61F 2/4081 623/19.13 |
| 2007/0255412 A1* | 11/2007 | Hajaj ............. A61F 2/38 623/17.11 |
| 2007/0299529 A1 | 12/2007 | Rhodes et al. |
| 2007/0299532 A1* | 12/2007 | Rhodes et al. ........... 623/20.32 |
| 2008/0027556 A1 | 1/2008 | Metzger |
| 2008/0027557 A1 | 1/2008 | Tuke |
| 2008/0058945 A1 | 3/2008 | Hajaj et al. |
| 2008/0091273 A1* | 4/2008 | Hazebrouck ............. 623/20.34 |
| 2008/0119938 A1 | 5/2008 | Oh |
| 2008/0133020 A1* | 6/2008 | Blackwell et al. ........ 623/20.34 |
| 2008/0139965 A1 | 6/2008 | Meneghini et al. |
| 2008/0183177 A1* | 7/2008 | Fox et al. ................. 606/88 |
| 2008/0183291 A1 | 7/2008 | Scheller et al. |
| 2008/0243259 A1* | 10/2008 | Lee et al. ............. 623/20.32 |
| 2009/0036984 A1 | 2/2009 | Hagen et al. |
| 2009/0118830 A1* | 5/2009 | Fell ............. 623/14.12 |
| 2009/0132047 A1 | 5/2009 | Mansmann et al. |
| 2009/0138021 A1 | 5/2009 | Colquhoun et al. |
| 2009/0210066 A1 | 8/2009 | Jasty |
| 2009/0216325 A1* | 8/2009 | May et al. ............. 623/11.11 |
| 2009/0226068 A1* | 9/2009 | Fitz et al. ............. 382/131 |
| 2009/0228114 A1* | 9/2009 | Clark et al. ............. 623/20.36 |
| 2009/0299481 A9 | 12/2009 | Romagnoli |
| 2009/0326667 A1 | 12/2009 | Williams et al. |
| 2010/0016981 A1 | 1/2010 | Roger |
| 2010/0094429 A1 | 4/2010 | Otto |
| 2010/0100190 A1 | 4/2010 | May et al. |
| 2010/0100191 A1 | 4/2010 | May et al. ............. 623/20.34 |
| 2010/0191341 A1 | 7/2010 | Byrd |
| 2010/0217395 A1* | 8/2010 | Bertagnoli ............. A61B 17/14 623/17.16 |
| 2010/0249941 A1* | 9/2010 | Fell ............. A61F 2/389 623/20.28 |
| 2010/0298947 A1 | 11/2010 | Unger |
| 2010/0305575 A1 | 12/2010 | Wilkinson et al. |
| 2010/0312350 A1 | 12/2010 | Bonutti |
| 2011/0004316 A1 | 1/2011 | Murray et al. |
| 2011/0015751 A1 | 1/2011 | Laird |
| 2011/0022179 A1 | 1/2011 | Andriacchi et al. |
| 2011/0029089 A1* | 2/2011 | Giuliani ............. A61F 2/40 623/19.14 |
| 2011/0029092 A1 | 2/2011 | Deruntz et al. |
| 2011/0035018 A1* | 2/2011 | Deffenbaugh et al. ..... 623/20.28 |
| 2011/0066246 A1* | 3/2011 | Ries et al. ............. 623/20.27 |
| 2011/0112650 A1 | 5/2011 | Masini |
| 2011/0178605 A1 | 7/2011 | Auger et al. |
| 2011/0178606 A1 | 7/2011 | Deffenbaugh et al. |
| 2011/0178607 A1 | 7/2011 | Oosthuizen |
| 2011/0184528 A1* | 7/2011 | Beckendorf et al. ...... 623/23.42 |
| 2011/0190898 A1* | 8/2011 | Lenz et al. ............. 623/20.32 |
| 2011/0218635 A1 | 9/2011 | Amis et al. |
| 2012/0016482 A1* | 1/2012 | Mooradian et al. ....... 623/18.11 |
| 2012/0022658 A1 | 1/2012 | Wentorf |
| 2012/0041564 A1* | 2/2012 | Landon ............. A61F 2/389 623/20.34 |
| 2012/0046752 A1 | 2/2012 | Blanchard et al. |
| 2012/0109324 A1 | 5/2012 | Keggi et al. |
| 2012/0116524 A1* | 5/2012 | Walker et al. ............. 623/20.35 |
| 2012/0136452 A1 | 5/2012 | Richter et al. |
| 2012/0191204 A1 | 7/2012 | Bae et al. |
| 2012/0209390 A1 | 8/2012 | Gosset et al. |
| 2012/0245699 A1 | 9/2012 | Lang et al. |
| 2012/0265315 A1* | 10/2012 | Kusogullari ............. A61F 2/4003 623/19.14 |
| 2012/0296436 A1* | 11/2012 | Klawitter et al. ......... 623/19.14 |
| 2012/0310361 A1 | 12/2012 | Zubok et al. |
| 2012/0330429 A1 | 12/2012 | Axelson, Jr. et al. |
| 2012/0330431 A1 | 12/2012 | Rolston |
| 2013/0018477 A1 | 1/2013 | Muratoglu et al. |
| 2013/0020733 A1* | 1/2013 | Berger ............. 264/40.1 |
| 2013/0030540 A1 | 1/2013 | Leibinger |
| 2013/0102929 A1 | 4/2013 | Haight et al. |
| 2013/0103159 A1 | 4/2013 | Andriacchi et al. |
| 2013/0144393 A1* | 6/2013 | Mutchler ............. A61F 2/4081 623/19.11 |
| 2013/0166037 A1* | 6/2013 | Goodfellow et al. ...... 623/20.32 |
| 2013/0204258 A1 | 8/2013 | Goodfellow et al. |
| 2013/0204384 A1* | 8/2013 | Hensley et al. ............ 623/20.35 |
| 2013/0218284 A1* | 8/2013 | Eickmann et al. ........ 623/20.34 |
| 2014/0128983 A1* | 5/2014 | Flaherty ............. A61F 2/4081 623/19.13 |
| 2014/0236308 A1* | 8/2014 | Oosthuizen ............. 623/20.28 |
| 2014/0243990 A1* | 8/2014 | Collazo et al. ............. 623/20.32 |
| 2014/0277520 A1* | 9/2014 | Chavarria et al. ......... 623/19.13 |
| 2014/0277528 A1* | 9/2014 | Mines et al. ............. 623/20.16 |
| 2014/0277539 A1* | 9/2014 | Cook et al. ............. 623/20.32 |
| 2014/0277548 A1* | 9/2014 | Cohen et al. ............. 623/20.34 |
| 2014/0296985 A1* | 10/2014 | Balasubramanian ... A61F 2/442 623/17.16 |
| 2014/0324179 A1* | 10/2014 | Salehi et al. ............. 623/20.32 |
| 2014/0343681 A1* | 11/2014 | Cohen et al. ............. 623/20.32 |
| 2015/0018956 A1* | 1/2015 | Steinmann ............. A61F 2/447 623/17.16 |
| 2015/0134063 A1* | 5/2015 | Steinmann ............. A61B 17/80 623/17.16 |

OTHER PUBLICATIONS

Bert et. al. A Comparison of the Mechanical Stability of Various Unicompartmental Tibial. Orthopedics; Jun. 1994; 17, 6; Proquest Central, p. 559.

Bloebaum et. al. Postmortem Analysis of Bone Growth Into Porous-Coated Acetabular Components. Journal of Bone and Joint Surgery; Jul. 1997; 79, 7; Proquest Central p. 1013.

Burton et. al. Computer-Assisted Fluoroguide Navigation of Unicompartmental Knee Arthroplasty. Can J Surg, vol. 52, No. 5, Oct. 2009.

Callaghan et. al. Mobile-Bearing Knee Replacement: Concepts and Results. Journal of Bone and Joint Surgery; Jul. 2000; 82, 7; Proquest Central p. 1020.

(56) References Cited

OTHER PUBLICATIONS

Collier et.al. Shelf Age of the Polyethylene Tibial Component and Outcome of Unicondylar Knee. Journal of Bone and Joint Surgery; Apr. 2004; 86, 4; Proquest Central p. 763.

Diezi et al. Effect of Femoral to Tibial Varus Mismatch on the Contact Area of Unicondylar Knee Prostheses. The Knee 17 (2010) 350-355.

Epinette et. al. Is Hydroxyapatite a Reliable Fixation Option in Unicompartmental Knee Arthroplasty? A 5- to 13-Year Experience With the Hydroxyapatite-Coated Unix Prosthesis. The Journal of Knee Surgery.

Forsythe et. al. Unicondylar Knee Arthroplasty: A Cementless Perspective. Canadian Journal of Surgery; Dec. 2000; 43, 6; Proquest Central p. 417.

Geller et. al. Unicompartmental Knee Arthroplasty: A Controversial History and a Rationale for Contemporary Resurgence. J Knee Surg. 2008; 21:7-14.

Hall et. al. Unicompartmental Knee Arthroplasty (Alias Uni-Knee): An Overview With Nursing Implications. Orthopaedic Nursing; May/Jun. 2004; 23, 3; Proquest Central,p. 163.

Harman et. al. Polyethylene Insert Damage in Unicondylar Knee Replacement: A comparison of in vivo function and in vitro simulation. A Proceedings of the Institution of Mechanical Engineers; 2010; 224, H7; Proquest Central, p. 823.

Hofmann et. al. Modular Uncemented Tricompartmental Total Knee Arthroplasty. A Comparison Between Posttraumatic and Nonposttraumatic Osteoarthrosis. European Journal of Trauma 2005 No. 2 © Urban & Vogel.

Kasisa et. al. The Precision and Accuracy of Templating the Size of Unicondylar Knee Arthroplasty. The Knee 11 (2004) 395-398.

Lavernia et al. Knee Arthroplasty: Growing Trends and Future Problems. Int. J. Clin. Rheumatol. (2010) 5(5), 565-579.

Lecuire et. al. Mid-Term Results of a New Cementless Hydroxyapatite Coated Anatomic Unicompartmental Knee Arthroplasty. Eur J Orthop Surg Traumatol (2008) 18:279-285. DOI 10.1007/S00590-008-0299-4.

Rosa et. al. An Evaluation of All-Ultra-High Molecular Weight Polyethylene Unicompartmental Tibial Component Cement-Fixation Mechanismslournal of Bone and Joint Surgery; 2002; 84, Proquest Central.

Saccomanni et. al. Unicompartmental Knee Arthroplasty: A Review of Literature. Clin Rheumatol (2010) 29:339-346; DOI 10.1007/S10067-009-1354-1.

Sanchis-Alfonso et al. Extensive Osteolytic Cystlike Area Associated With Polyethylene Wear Debris Adjacent to an Aseptic, Stable, Uncemented Unicompartmental Knee Prosthesis: Case Report. Knee Surg, Sports Traumatol, Arthrosc, (2001) 9 :173-177.

Soininvaara et. al. Periprosthetic Bone Mineral Density Changes After Unicondylar Knee Arthroplasty. The Knee 20 (2013) 120-127.

Sorrells et. al. The Clinical History and Development of the Low Contact Stress Total Knee Arthroplasty. Orthopedics; Feb. 2002; 25, 2; Proquest Central p. S207.

Sorrells et. al. The Rotating Platform Mobile Bearing TKA. Orthopedics; Sep. 1996; 19, 9; Proquest Central, p. 793.

Suero et. al. Effects of Tibial Slope Changes in the Stability of Fixed Bearing Medial Unicompartmental Arthroplasty in Anterior Cruciate Ligament Deficient Knees. The Knee 19 (2012) 365-369.

Tanavalee et. al. Unicondylar Knee Arthroplasty: Past and Present. Orthopedics; Dec. 2005; 28, 12; Proquest Central, p. 1423.

Whiteside et al. Effect of Porous-Coating Configuration on Tibial Osteolysis After Total Knee Arthroplasty. Clinical Orthopaedics & Related Research: Dec. 1995.

International Search Report and Written Opinion for Application No. PCT/US2014/027827 dated Jun. 25, 2014.

\* cited by examiner

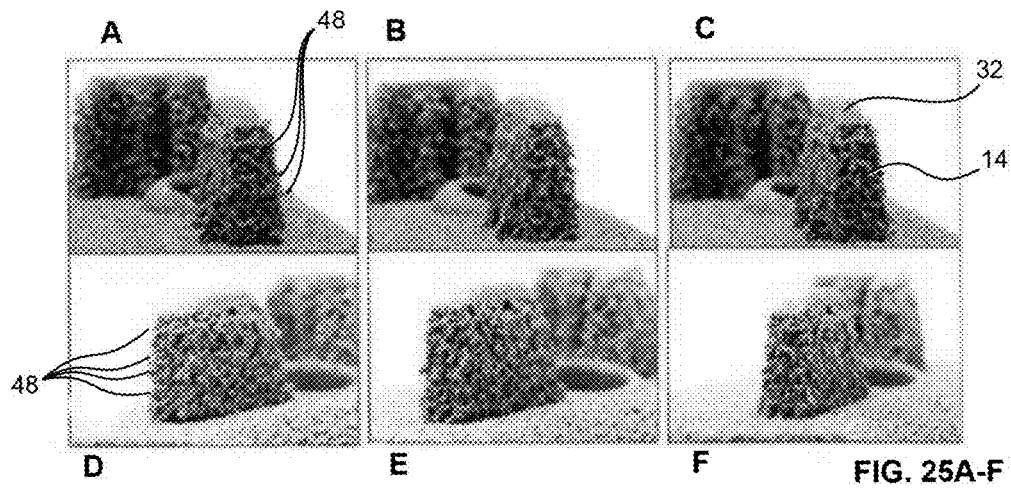
FIG. 25A-F
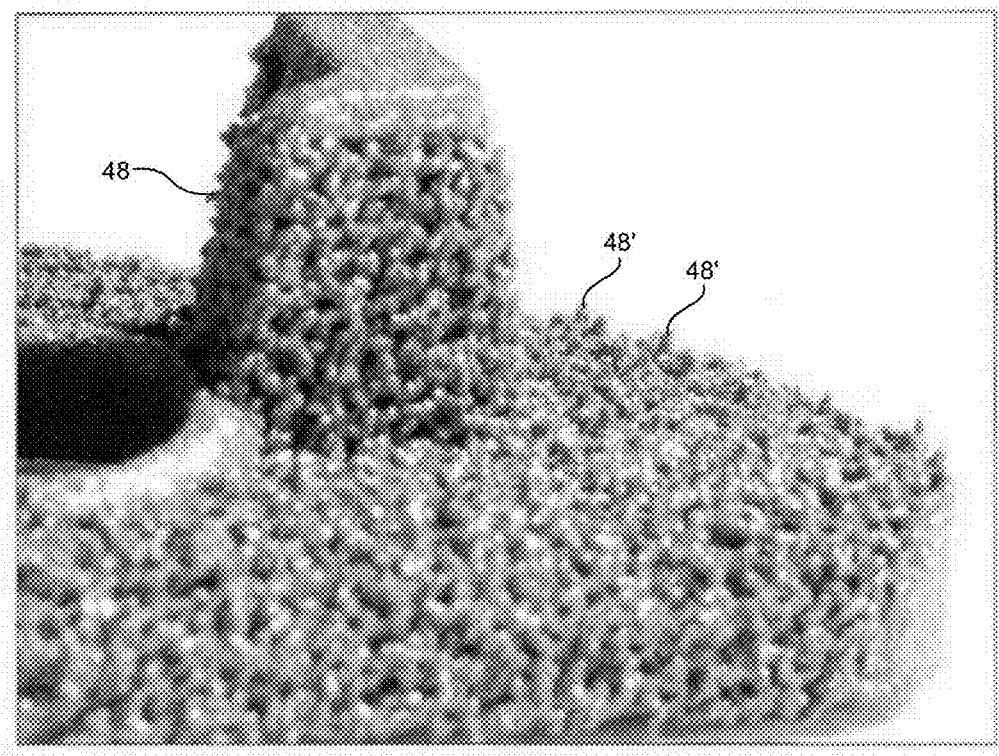
FIG. 26

UNICONDYLAR TIBIAL KNEE IMPLANT

CROSS-REFERENCE TO RELATED APPLICATIONS

The present application claims the benefit of the filing date of U.S. Provisional Patent Application No. 61/794,339 filed Mar. 15, 2013, the disclosure of which is hereby incorporated herein by reference.

BACKGROUND OF THE INVENTION

The present invention relates generally to orthopedic implants. In particular, the present invention is discussed in connection with the tibial component of a unicondylar knee implant system, although the invention is not limited to just that type of component.

Orthopedic knee implant systems have been used for many years to treat patients with knee joints that have been damaged by trauma or disease, such as osteoarthritis, rheumatoid arthritis, and avascular neurosis. A knee arthroplasty procedure generally involves resecting, cutting, or resurfacing the damaged sections of the knee and replacing them with an endoprosthetic or implant.

Most knee implant systems are tricompartmental or total implants and the surgical procedure used with such implants is commonly known as total knee arthroplasty. These implants are known as tricompartmental implants because they are used when the knee joint is prepared to receive an implant by resurfacing or resecting the three articulating compartments, i.e., the medial and lateral femorotibial and the patellofemoral surfaces. Regardless of the type of implant used, arthroplasties generally require the bone to be specifically prepared to receive a corresponding implant by resecting, cutting, resurfacing, or otherwise deforming the bone to accept the implant.

Unicondylar or unicompartmental knee implants have become of great interest in the orthopedic industry due to their less invasive nature and the maintaining of the other healthy knee compartments. Unicondylar knees typically resurface or resect the medial or lateral femorotibial articulating surfaces thus allowing preservation of the other compartments not suffering from damage due to trauma or disease.

Historically, orthopedic devices have been mated with host bone by cementing them in place using methyl methacrylate, generally termed bone cement. The use of bone cement in attaching a prosthesis within or onto a prepared bone provides an excellent immediate fixation but has various disadvantages that appear over time. Physical loads are repeatedly applied to the implant over its life. If bone cement is used to secure a unicompartmental knee prosthesis, the bone cement may fatigue and fracture under the repeated loading. In some instances, degradation of the bone cement integrity may cause the device to become loose, thereby necessitating replacement. Old bone cement must be removed from the host bone as part of the implant replacement procedure. This procedure can be complex, time consuming and potentially destructive to healthy bone structures surrounding the implant. Furthermore, conventional bone cement is cured after it has been dispensed into the patient's joint. Loose undetected cement fragments can remain in the joint space and, with patient mobility over time, increase the degradation rate of articulating implant surfaces.

More recently, the development of orthopedic implant designs has moved towards satisfying the requirements of high demand patients. Patients today require more from their implants, and because patients are living longer, they require implants that to last longer. Accordingly, developments have been made in materials used to make orthopedic implants to improve implant longevity, such as highly porous metals that improve biological bone fixation. These implants are generally termed press-fit or cementless.

Recognizing the disadvantages of cement fixation techniques, prior art devices have also been developed that utilize other mechanical attachment means to join an implant to bone for immediate stabilization. Although various implant surface treatments intended to bond with bone biologically for long term stable attachment have proven successful, an initial fixation and stabilization is required before the bone growth can occur. A simple technique of mechanically securing an implant, is to affix it within the bone with screws or other mechanical fasteners. However, due to the nature of the bone surrounding the surgical site, and other limiting factors such as artery location and the like, screws can only be applied in certain limited regions. The use of a screw for implant fixation should be considered only as an option by the surgeon depending upon implant placement and bone quality.

Therefore, there exists a need for an improved implant design that provides both short term and long term fixation and stabilization.

BRIEF SUMMARY OF THE INVENTION

The present invention is described below in connection with the preferred embodiment unicondylar tibial implant. However, the present invention has applicability to other orthopedic implants, including unicondylar femoral implants and even total implants. For instance, the below description of the present invention is provided for a tibial implant to be used on the medial condyle. However, the preferred embodiment can also be used on the lateral condyle, and when utilized in such a manner would have some features reversed in orientation. A description of the medial component features of the tibial implant is provided only for simplification.

In accordance with a preferred embodiment, the present invention provides for a unicondylar tibial implant. The tibial implant includes a tibial keel positioned on a surface of the tibial implant to be submerged into prepared bone with a first projection extending along its lengthwise direction and a second projection extending along a direction perpendicular to the first projection. The first projection may be interrupted by a void to allow clearance for another implant or instrument. The second projection intersects the first projection. The tibial implant can be fabricated from a metal, a polymer, a biodegradable material, a porous metal material, or combinations thereof. The device as described could be produced through additive manufacturing techniques such as direct metal laser sintering.

The tibial keel is configured as an anterior-posterior projection with an intersecting keel segment that extends about a medial-lateral direction. The tibial keel is comprised of a solid material on a bone interfacing leading edge of the tibial keel i.e., a solid end portion, with the tibial keel having a porous material between the tibial tray and the solid end portion of the tibial keel. The tibial implant can optionally include a bone screw to secure the tibial implant to bone.

In accordance with another preferred embodiment, the present invention provides for a unicondylar tibial implant having a tibial keel configured as an anterior-posterior projection with at its most anterior aspect being an intersecting keel in the medial-lateral direction. The tibial keel is comprised of a solid material on a leading edge of the keel and porous material between the tibial tray and the solid end portion of the keel, and smaller protrusions on the medial facing portion of the tibial keel at the intersection of the tibial keel and tibial tray. The tibial implant is fabricated from a metal, a polymer and/or a biodegradable material. The tibial implant can optionally include a bone screw to secure the tibial implant to bone.

In accordance with yet another preferred embodiment, the present invention provides for a unicondylar tibial implant having a tibial keel configured as an anterior-posterior projection with at its most anterior aspect being an intersecting keel in the medial-lateral direction. The tibial keel is comprised of a solid material on the leading edge of the keel and porous material between the tibial tray and a solid end portion of the keel being implanted into an interference-fit created by an undersized preparation in the bone. The tibial implant is fabricated from a metal, a polymer and/or a biodegradable material. The tibial implant can optionally include a bone screw to secure the tibial implant to bone.

In accordance with another preferred embodiment, the present invention provides for a unicondylar tibial implant having a tibial keel configured as an anterior-posterior projection with at its most anterior aspect being an intersecting keel in the medial-lateral direction. The tibial keel is comprised of a solid material on a leading edge of the keel and porous material between the tibial tray and a solid end portion of the keel, and smaller protrusions on the medial facing portion of the keel at the intersection of the tibial keel and tibial tray where the protrusions preferentially force the tibial implant into the bone prepared about a resected mid-tibial eminence. The tibial implant is implanted into an interference fit created by an undersized preparation in the bone. The tibial implant is fabricated from a metal, a polymer and/or a biodegradable material. The tibial implant can optionally include a bone screw to secure the tibial implant to bone.

In accordance with yet another preferred embodiment, the present invention provides for a keel for a unicondylar tibial implant. The keel is connected to the tibial tray of the tibial implant and includes smaller protrusions on a medial facing portion of the keel at an intersection of the keel and the tibial tray where the protrusions push the tibial implant into the bone prepared about a resected tibial eminence. The keel is fabricated from a metal, a polymer and/or a biodegradable material. The tibial implant can optionally include a bone screw to secure the tibial implant to bone.

In accordance with another preferred embodiment, the present invention provides for a unicondylar tibial implant having a tibial tray with a porous keel and protrusions extending from the keel. The tibial tray accepts a polyethylene tibial bearing having an articulating surface for articulating with a femoral component. The tibial bearing can be a modular polyethylene tibial bearing. The tibial implant and tibial bearing can also be formed as a monoblock component. Alternatively, the tibial tray with a porous keel can be formed out of a singular biomaterial which is also used to form the tibial bearing. The tibial implant can optionally include a bone screw to secure the tibial implant to bone.

In accordance with yet another preferred embodiment, the present invention provides for a unicondylar tibial implant having at least one section of material that in its normal state forms at least one uninterrupted surface of the tibial implant that is separable from the greater bulk of the tibial implant in a predictable shape defined by the presence of a shear section. The shear section of material when removed exposes a passageway for at least one additional implant, such as a bone screw. The removal of the shear section also exposes a passageway for surgical instrumentation, for the application of osteobiologic materials or for the application of bone cement.

In accordance with another preferred embodiment, the present invention provides for the ornamental design of a unicondylar tibial implant as shown and described in the figures below.

Another embodiment of the present invention is an orthopedic implant for replacing a portion of a bone including a bone contacting surface and a keel extending from the bone contacting surface. The keel includes a first projection with a first longitudinal axis and a second projection with a second projection with a second longitudinal axis. The first and second longitudinal axes are oriented orthogonally to each other. The hole may be configured to accept a bone screw at a plurality of different angles, and the first and second projections may be separated from each other by the hole. The hole may include a plug removable upon the application of a force. At least one fin may be associated with the first projection and extend oblique to the first longitudinal axis. That fin may be shaped to engage the bone, and/or configured to enter into an unprepared portion of the bone. At least one extension may be associated with the second projection and extend oblique to the second longitudinal axis. That extension may be shaped to engage the bone, and/or frictionally engage the bone. The implant may further include a porous portion adapted to allow for the bone to grow therein. The porous portion may cover at least a portion of the bone contacting surface and at least a portion of the keel, and the keel may include a solid portion at a distal end of the keel. The porous portion may define a first porous surface and at least one boundary strut extending from the surface in a first direction. The boundary strut may extend any angle, including from 0 to 10 degrees from normal to the first porous surface. The implant may also further include a third projection, as well as a bearing component attachable to the implant. In certain embodiments, the implant is a unicondylar tibial baseplate, and a kit including the implant may include at least one other implant.

Yet another embodiment of the present invention is a tibial baseplate including a bone contacting surface having anterior, posterior, medial and lateral sides, a first projection extending from the bone contacting surface and having a first length extending in a first direction between the anterior and posterior ends, a second projection extending from the bone contacting surface and having a second length extending in a second direction between the medial and lateral sides, an aperture for receiving a bone screw and a porous material for promoting bone ingrowth, the porous material at least partially covering the bone contacting surface, the first projection and the second projection. The baseplate may further include a third projection. The porous material may define a plurality of boundary struts extending from the bone contacting surface in a first direction at between 0 to 10 degrees from normal to the bone contacting surface. The first and second projections may be separated from each other by the aperture. The aperture may be configured to accept a bone screw at a plurality of different angles, and may include a plug removable upon the application of a force. At least one fin or extension may be associated with at least one of the first and second projections, where the fin is configured to enter into an unprepared portion of the bone and the extension frictionally engages the bone. A solid portion may be included at distal ends of the first and second projections.

A still further embodiment is a tibial baseplate including a bone contacting surface having anterior, posterior, medial and lateral sides, a first projection extending from the bone contacting surface and having a first length extending in a first direction between the anterior and posterior ends, a second projection extending from the bone contacting surface and having a second length extending in a second direction between the medial and lateral sides, an aperture for receiving a bone screw, a plug at least partially covering the aperture, the plug being removable upon the application of a force and a porous material for promoting bone ingrowth, the porous material at least partially covering the bone contacting surface, the first projection and the second projection, wherein the porous material defines a plurality of boundary struts extending from the bone contacting surface from 0 to 10 degrees from normal to the bone contacting surface.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Referring to the figures, wherein like reference numerals represent like parts throughout the several views:

FIGS. 21-29 are highly magnified photographic images of from a bottom perspective of a porous portion of the unicondylar tibial implant of FIG. 9.

DETAILED DESCRIPTION OF THE INVENTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that slight deviations from absolute are included within the scope of the term so modified. Likewise, for purposes of convenience and clarity only, directional terms such as top, bottom, above, below and diagonal, may be used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Figure 9:
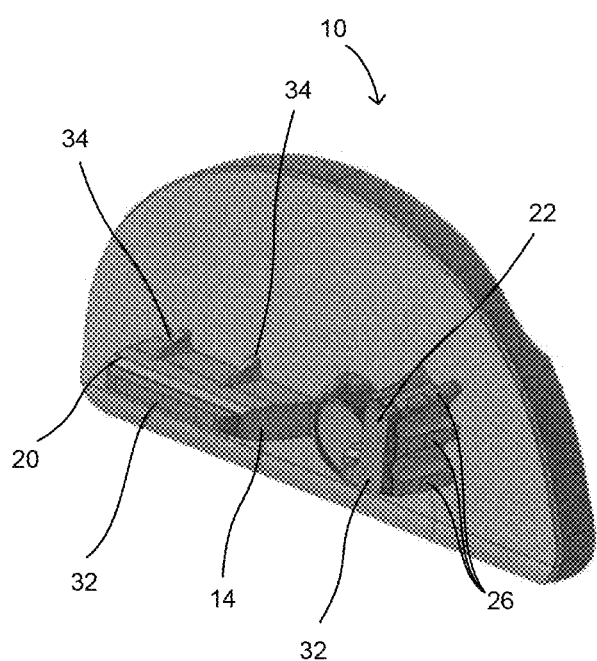
FIG. 9 is a bottom perspective view of a unicondylar tibial implant of the tibial implant assembly of FIGS. 1-8.
Figure 10:
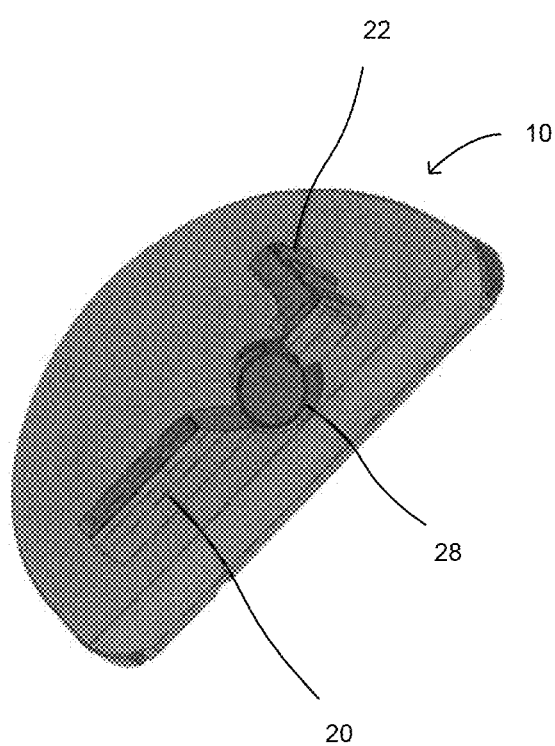
FIG. 10 is another bottom perspective view of the unicondylar tibial implant of FIG. 9.
Figure 11:
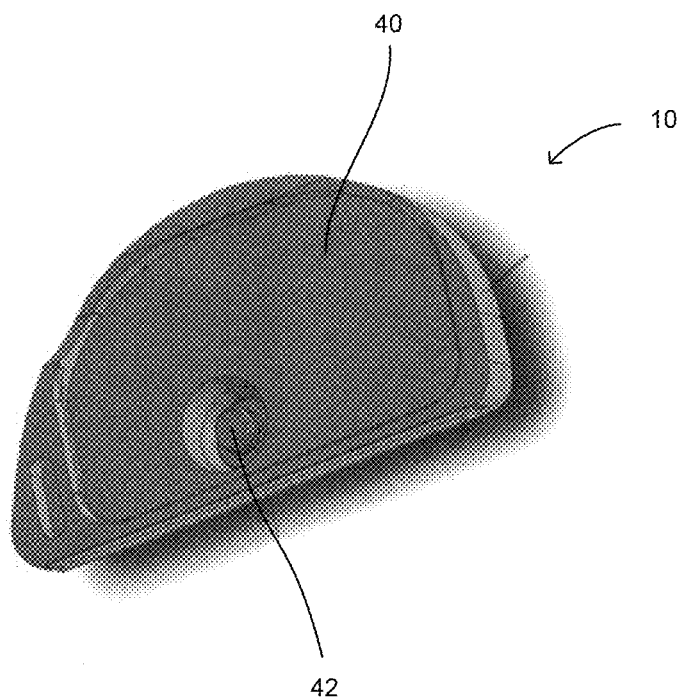
FIG. 11 is a top perspective view of the unicondylar tibial implant of FIG. 9.
Figure 12:
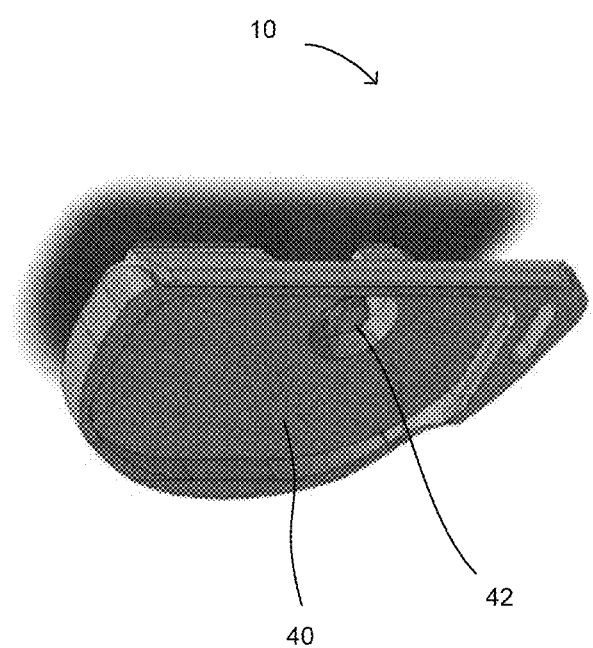
FIG. 12 is another top perspective view of the unicondylar tibial implant of FIG. 9.
Figure 13:
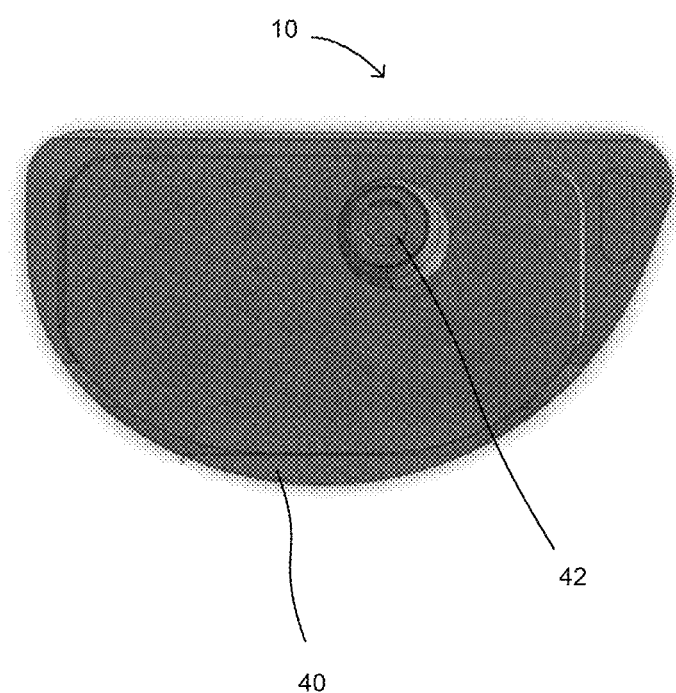
FIG. 13 is a top view of the unicondylar tibial implant of FIG. 9.
Figure 14:
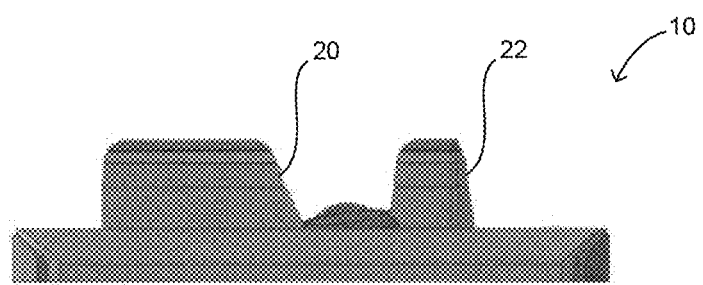
FIG. 14 is a side view of the unicondylar tibial implant of FIG. 9.
Figure 15:
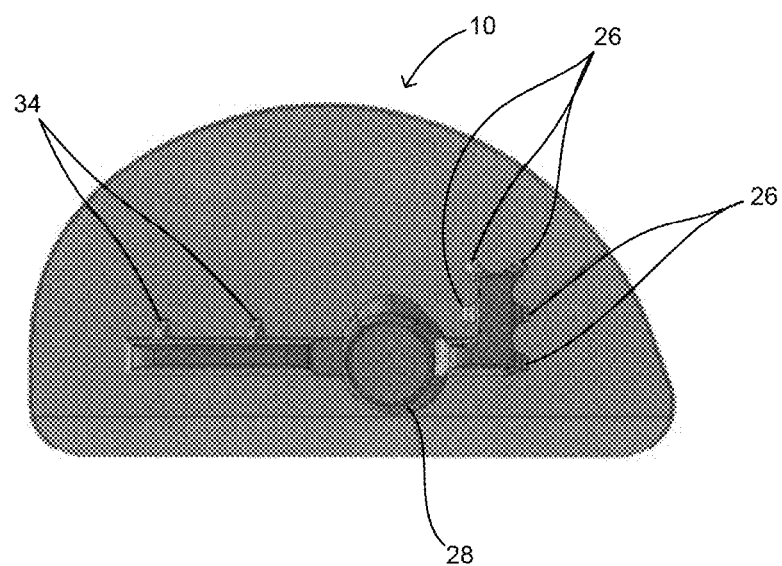
FIG. 15 is a bottom view of the unicondylar tibial implant of FIG. 9.
Figure 16:
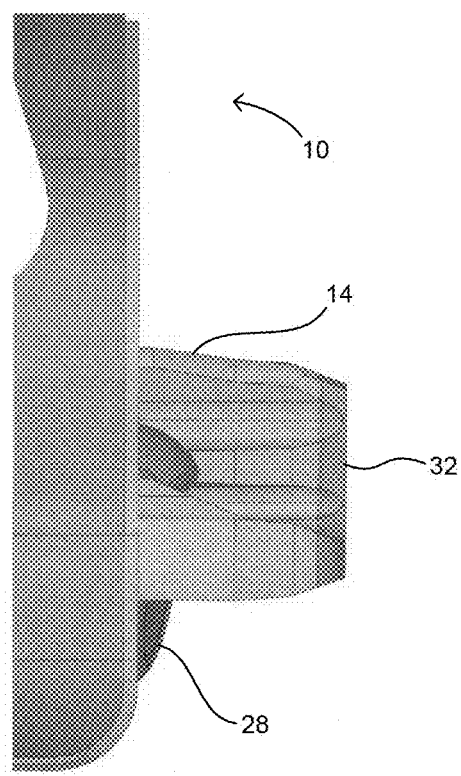
FIG. 16 is a front view of the unicondylar tibial implant of FIG. 9.
Figure 17:
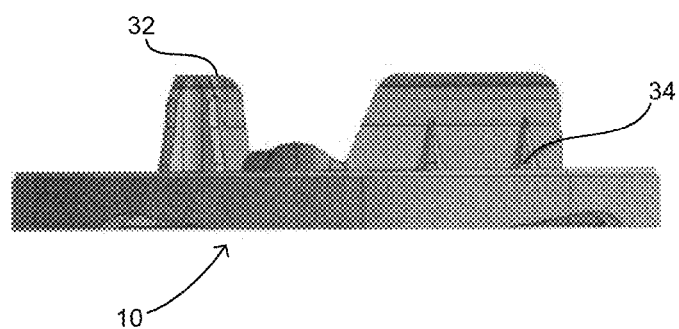
FIG. 17 is an opposite side view of that shown in FIG. 15.
Figure 18:
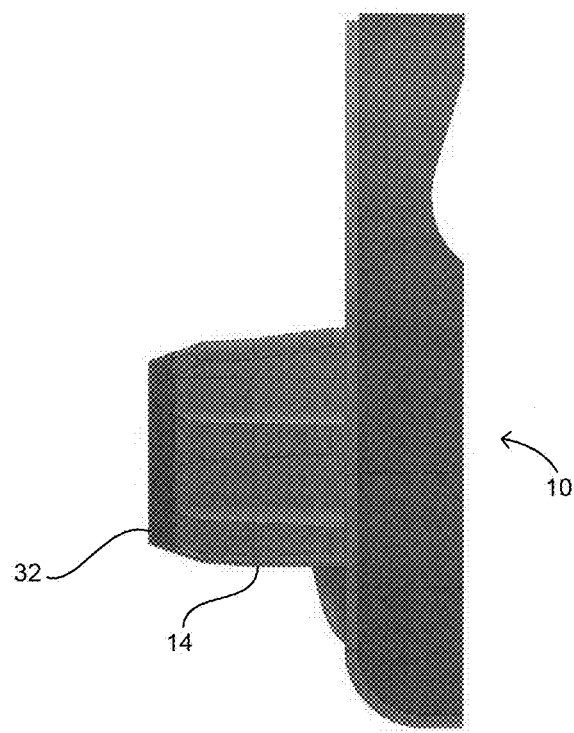
FIG. 18 is a rear view of the unicondylar tibial implant of FIG. 9.
Figure 30:
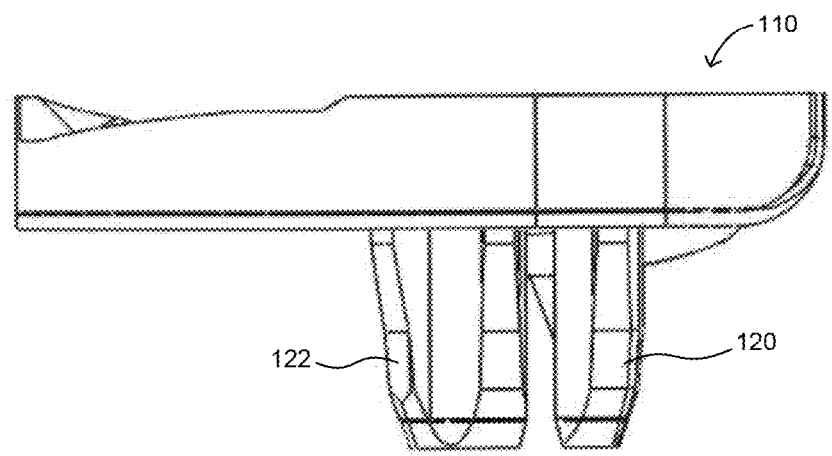
FIG. 30 is a side view of a unicondylar tibial implant in accordance with another embodiment of the present invention.
Figure 31:
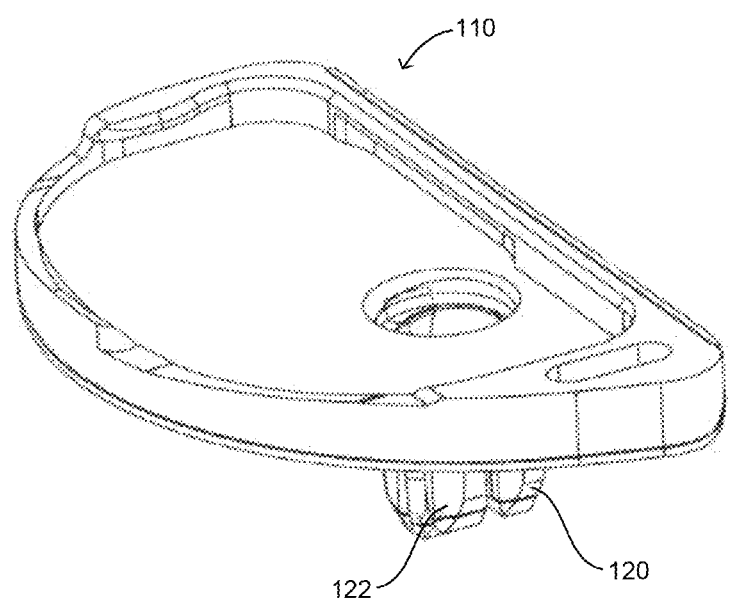
FIG. 31 is a top perspective view of the unicondylar tibial implant of FIG. 30.

Reference will now be made in detail to the preferred embodiments of the present invention illustrated in the accompanying drawings. Generally, the same or like reference numbers will be used throughout the drawings to refer to the same or like features, but within a different 100-series of numbers. For instance, FIG. 9 depicts a unicondylar tibial implant 10, while FIG. 30 depicts another embodiment unicondylar tibial implant 110. It should be noted that the drawings are in simplified form and are not drawn to precise scale.

As noted above, partial knee implants, also known as unicondylar or unicompartmental knee implants, are designed to replace either a medial or lateral compartment of a knee joint. A unicondylar replacement assembly may include a tibial implant (as is discussed below), either by itself or in conjunction with an implant designed to replace a femoral condyle. The preparation of the bone to accept such implants may be facilitated by instrumentation such as bone files, burrs, saws, punches, computer and/or robot assisted instrumentation/navigation systems. Once the bone is prepared, the implant may be secured to the bone by different means, including bone cement which bonds to the implant and impregnates the bone resulting in fixation of the implant to the bone interface.

The present invention has been designed to facilitate fixation directly to the bone, i.e. without bone cement. Such fixation without bone cement is known as cementless fixation or press-fit fixation. The present invention addresses the challenge of cementless fixation of implant components, which is to have acceptable initial stability upon implantation to allow patient mobility immediately or a short time after surgery and promote adequate biologic fixation of the implant to the bone long term. The initial stability and long term fixation are requirements of the implant to reduce the incidence of implant loosening and reduce patient post-operative pain over time.

The present invention of FIGS. 1-32 includes several different embodiments of a unicondylar tibial implant assembly 5 having a unicondylar tibial implant, tibial tray or baseplate 10 and a unicondylar tibial implant bearing 12. Of course, as noted above, although described in connection with a unicondylar implant for the tibia, the present invention has applicability to other types of implants. For instance, the present invention may be applied in unicondylar implant for the femur or even total implants. The unicondylar tibial implant 10 has been developed primarily for cementless application and includes a unique bone interfacing tibial keel 14 and a porous structured biomaterial interface i.e., a porous portion 16 (best shown in FIGS. 21-29). The tibial implant 10 can be constructed from any combination of solid metal, porous metal, polymers and/or other resorbable materials. For instance, it is contemplated to form the bearing 12 of a polymer material such as PEEK, and the implant 10 of a metal such as titanium or stainless steel. Likewise, it is contemplated to form implant 10 of different materials, e.g., porous portion 16 may be formed of a different material than the remainder of the implant.

For purposes of convenience only, and not by way of limitation, the foregoing description of the preferred embodiments of the unicondylar tibial implant assembly 5 will be described and illustrated with respect to a unicondylar tibial implant assembly 5 for a medial tibial condyle. However, the foregoing description and features of the unicondylar tibial implant assembly 5 are equally applicable to a unicondylar tibial implant assembly for a lateral condyle, such similar features of the lateral unicondylar tibial implant assembly being substantially mirror images of such features of the medial unicondylar tibial implant assembly. Of course, it is also contemplated that the medial and lateral versions of the assembly may be of a different construction to accommodate the different bony anatomy of the medial and lateral portions of the tibia.

The tibial keel 14 is preferably constructed of a combination of solid and porous portions and located on an undersurface or bottom of the tibial implant 10, which is designed to contact a resected tibia bone (not shown). The tibial keel 14 is generally submerged into the bone when the tibial implant 10 is implanted thereon. The tibial keel 14 can prepare its own cavity in the bone as it is inserted into the resected tibia or it can occupy cavities within the bone previously prepared by instrumentation or other implants. Any pre-cavities for receiving the tibial keel 14 when pre-prepared are generally smaller in size than the tibial keel 14 so as to generate compressive forces between the bone interface and the tibial keel 14 and increase frictional forces between the bone and the tibial keel 14. That is, the tibial keel 14 is press-fitted into the bone.

The tibial keel 14 is shown in FIGS. 2, 4-10 and 14-20 and includes a first projection or protrusion 20, which is generally planar and has a height which corresponds to a depth within a prepared bone to which the tibial keel 14 will protrude into, and a second projection or protrusion 22, which is also generally planar, has a height which corresponds to a depth within a prepared bone to which the tibial keel 14 will protrude into and is substantially perpendicular to the first projection 20 (i.e., the longitudinal axes of projections 20, 22 are orthogonally arranged). For purposes of clarification, projections 20, 22 are labeled with reference numeral 14 in FIG. 2 and reference numerals 20 or 22 in the remainder of the figures pertaining to implant 10.

The heights of first and second projections 20, 22 of the tibial keel 14 may be variable to accommodate access limitations while maximizing the fixation of the tibial implant 10 into bone. Preferably, the tibial keel 14 is positioned on an underside or inferior surface 24 of the tibial tray 10 with the first projection 20 running along the anterior-posterior direction, and the second projection 22 running along the medial-lateral direction. This results in the intersection of the longitudinal axes of the projections 20, 22. Both of the first and second projections 20, 22 of the tibial keel are substantially normal to the underside of the tibial tray 10, but this can vary in other embodiments. Further, although shown with a constant height (see e.g., FIG. 4), projections 20, 22 can be configured to have a height that varies along its length. In fact, in a later embodiment (FIG. 32), a projection similar to projection 20 is shown with a sloped configuration.

Figure 1:
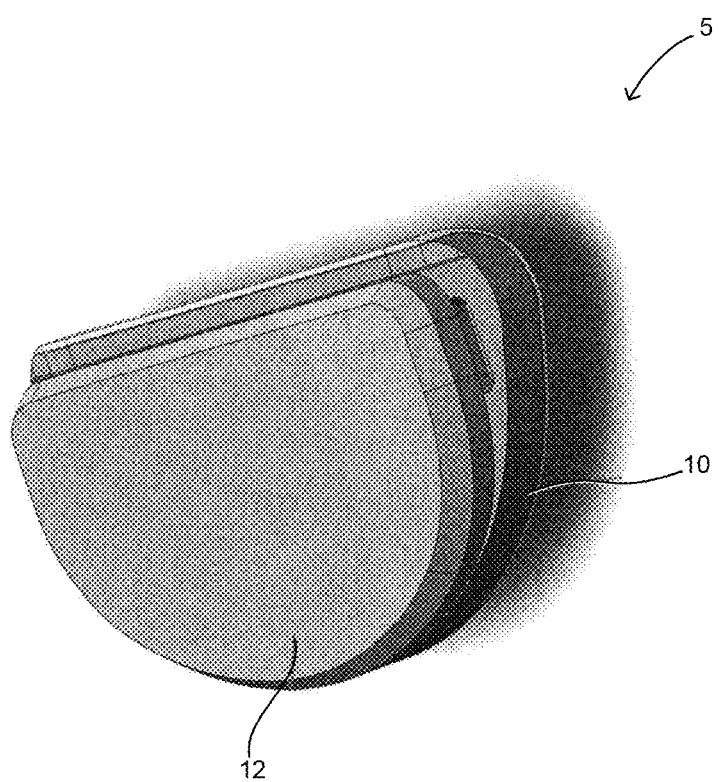
FIG. 1 is a top perspective view of a unicondylar tibial implant assembly in accordance with a preferred embodiment of the present invention.
Figure 2:
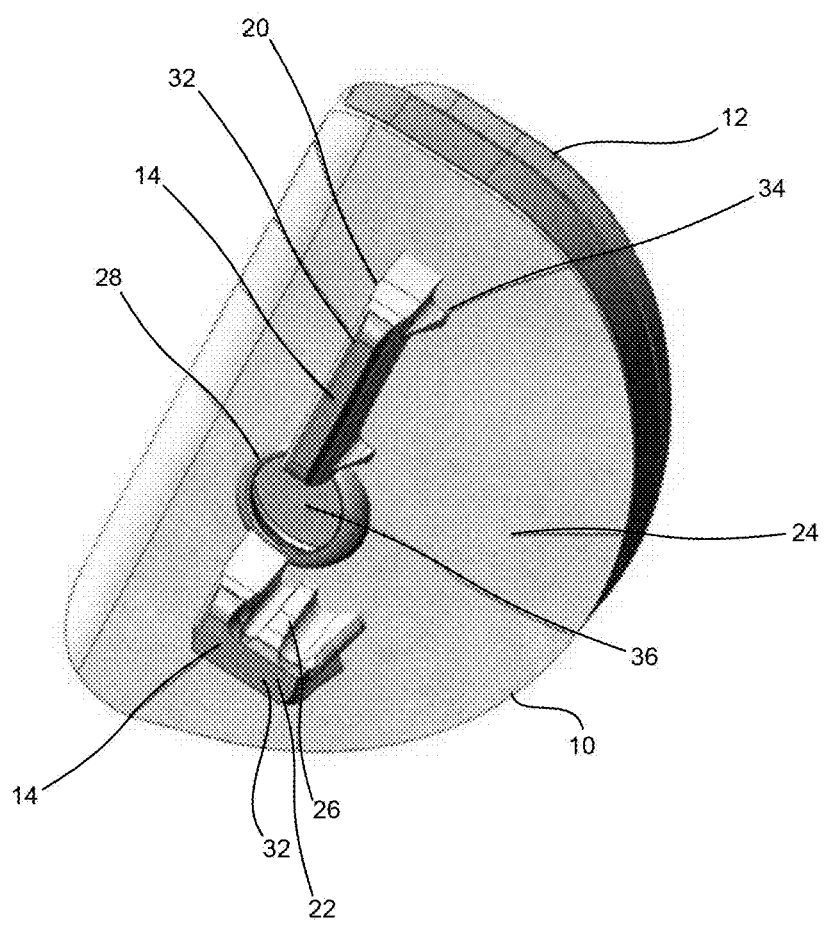
FIG. 2 is a bottom perspective view of the unicondylar tibial implant of FIG. 1.
Figure 3:
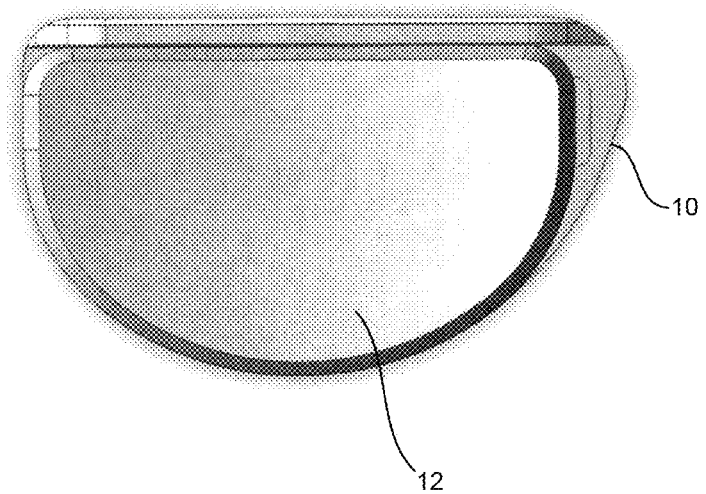
FIG. 3 is a top view of the unicondylar tibial implant of FIG. 1.
Figure 4:
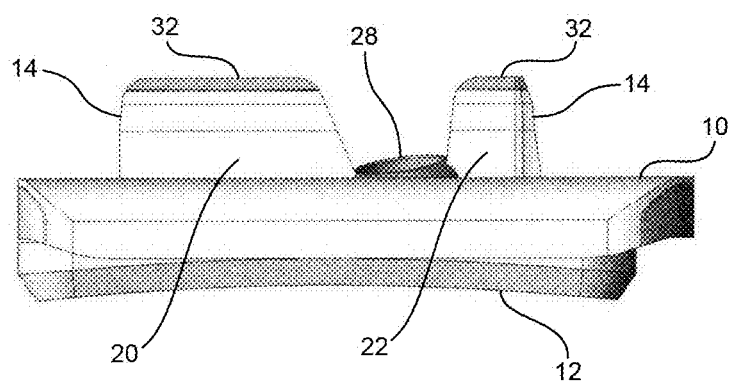
FIG. 4 is a side view of the unicondylar tibial implant of FIG. 1.
Figure 5:
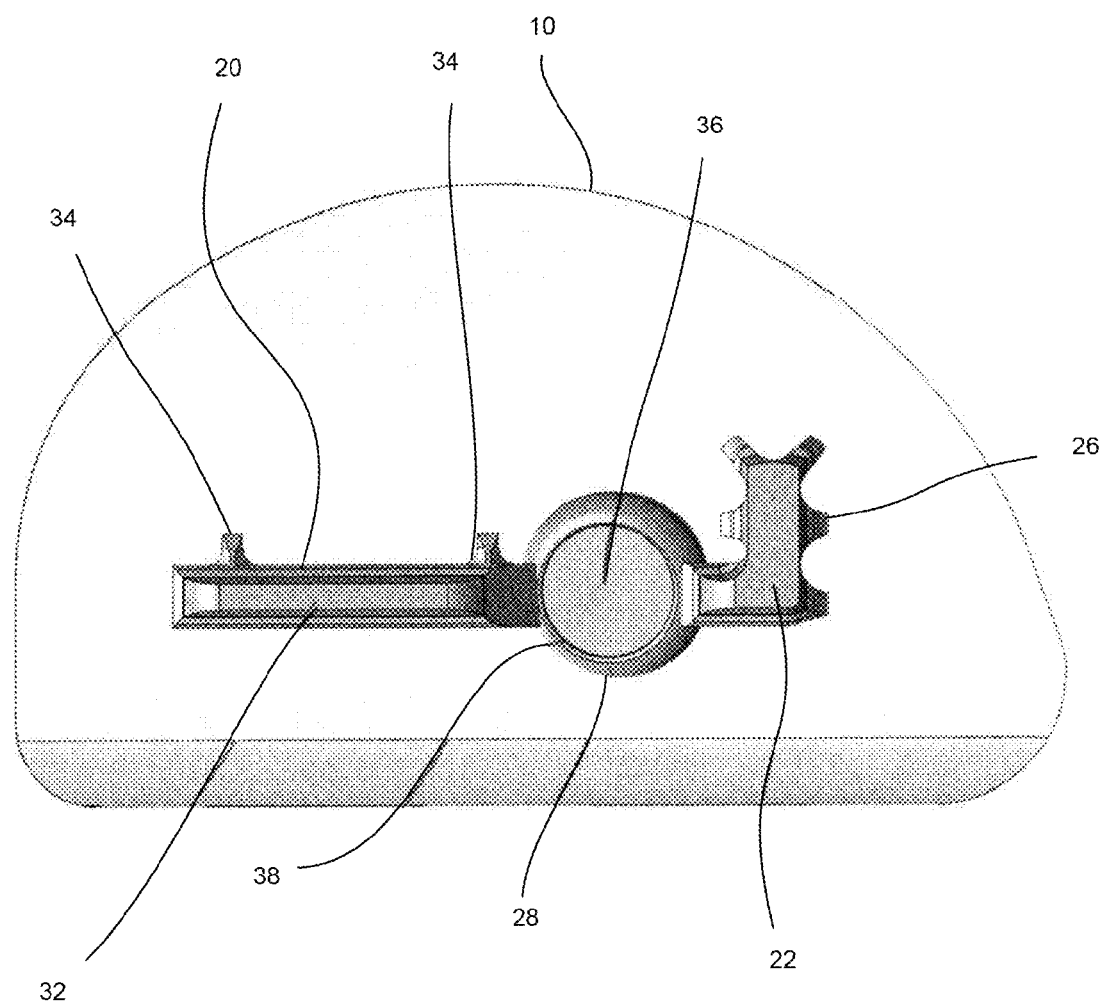
FIG. 5 is a bottom view of the unicondylar tibial implant of FIG. 1.
Figure 6:
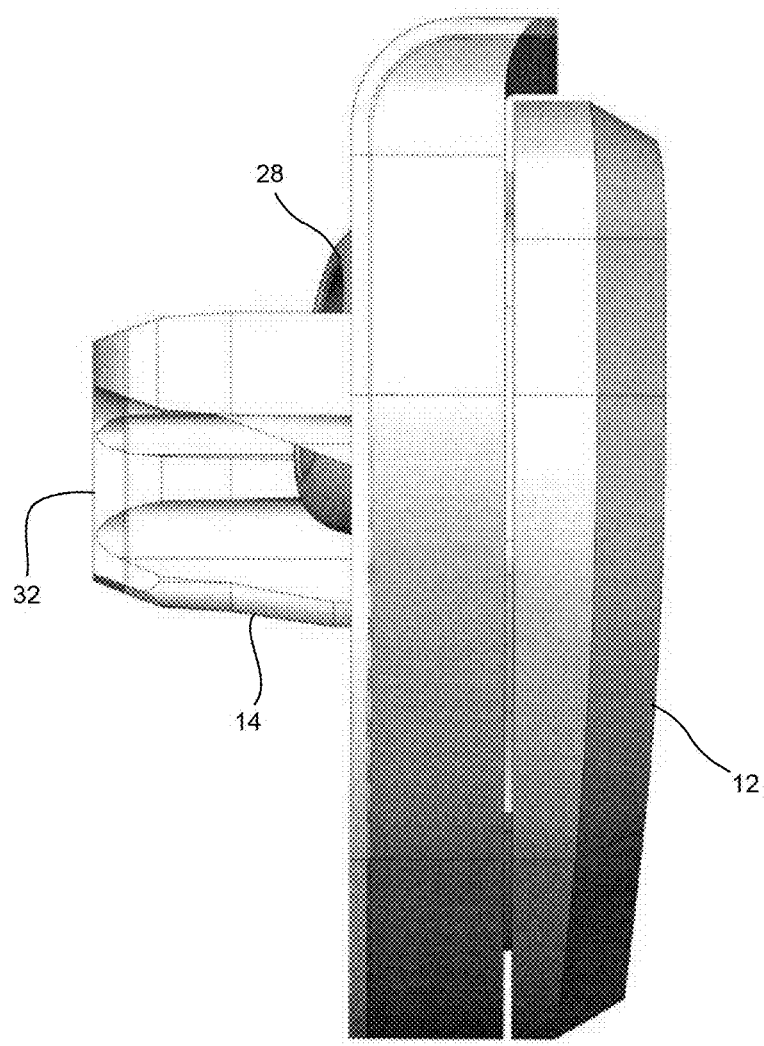
FIG. 6 is a front view of the unicondylar tibial implant of FIG. 1.

Each of the first and second projections 20, 22 of the tibial implant 10 can be configured to have one or more extensions i.e., a plurality of extensions 26 shown in FIGS. 2 and 5 extending from the second projection 22. The extensions 26 that emanate from the projections are oriented out of plane with the projection. That is, the extensions 26 extend outwardly from the lateral surfaces of the projections. The extensions 26 are designed to create and/or fill cavities within the bone so as to create and/or maximize compressive frictional forces between the tibial keel 14 and the surrounding bone. The extensions 26 are preferably located so that resultant forces during insertion of the tibial implant 10 into a resected tibia bias the position of the tibial implant 10 in a predetermined or desired direction. The extensions 26 are configured as substantially wedge shaped extensions that extend along substantially the entire height of the keel, and are preferably tapered in the distal direction. The extensions 26 on the second projection 22 are spaced apart from each other and substantially circumscribe the second projection 22. Preferably, the second projection includes five extensions 26, but can include more or less than five.

The extensions 26 are preferably located around the periphery of both the first and second projections 20, 22 with a higher number of extensions 26 or higher density of extensions 26 emanating from the second projection 22 located about the anterior region of the tibial implant 10 where higher frictional forces are able to make a greater contribution to address anterior lift-off stability issues of the tibial implant 10 when implanted within the bone. The number of extensions 26 is greater on the sides of the projection 22 that face away from a central region of the tibial implant 10 so that bone reaction forces will push/direct the tibial implant 10 into the central region of the tibia.

Figure 7:
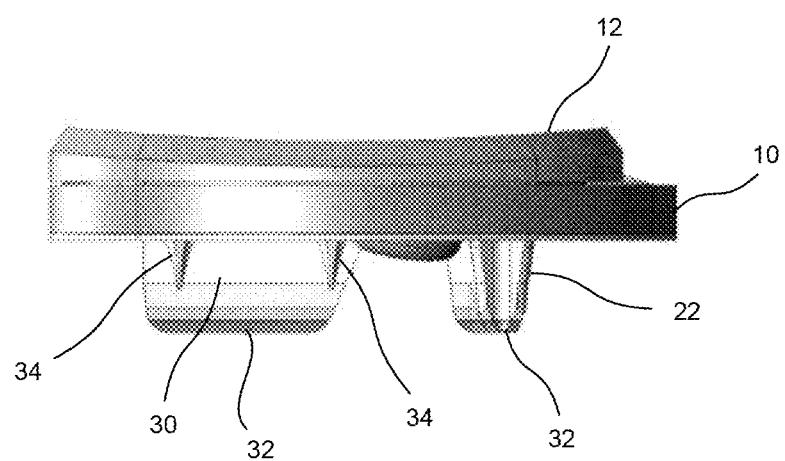
FIG. 7 is an opposite side view of that shown in FIG. 4.
Figure 8:
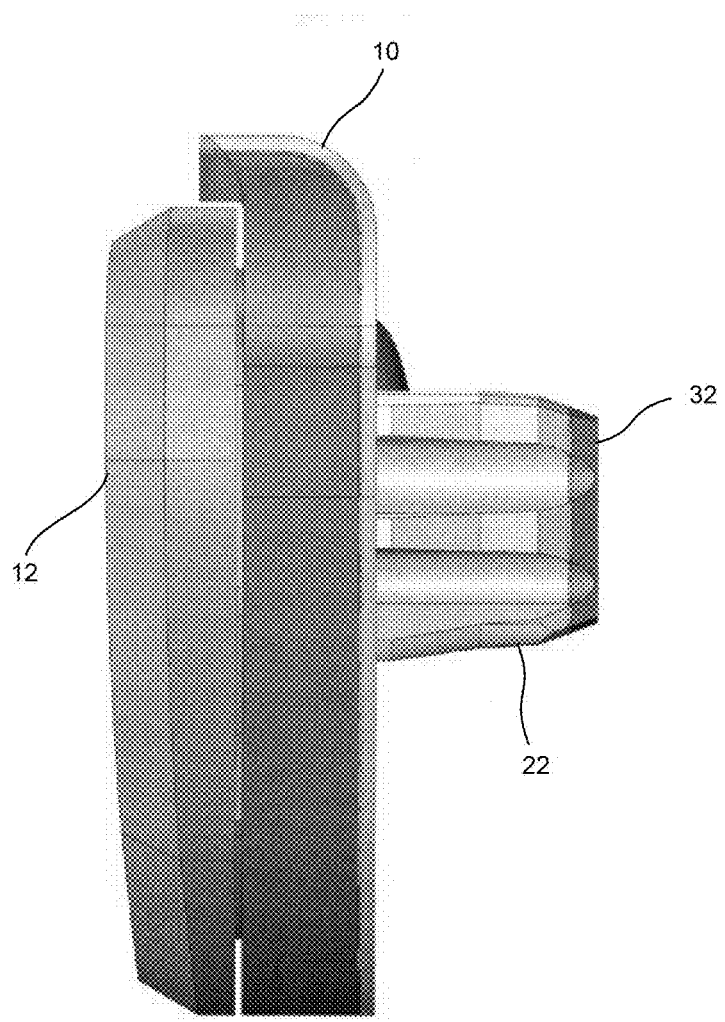
FIG. 8 is a rear view of the unicondylar tibial implant of FIG. 1.

The tibial keel 14 also includes a plurality of fins 34 which extend beyond the nominal volume of the tibial keel 14, specifically with respect to projection 20. The fins 34 enter bone that has not been prepared to receive the fins 34. Instead, the fins 34 prepare their own receiving volume within the bone as they are inserted into the bone, i.e., the fins 34 displace bone as they are placed therein. In other words, the fins 34 are inserted into bone without the need to prepare the bone to receive such fins 34. The fins 34 are sized to maximize their surface area, minimize their volume and are shaped to ease entry into the bone. For instance, as shown in FIGS. 2 and 7, the fins 34 are preferably configured as shown and are substantially wedge shaped or shaped as a dual inclined plane structure. Further, the fins 34 are tapered as they extend from a proximal end of the tibial keel 14 distally. The fins 34 are also preferably configured to extend an overall length about half way the overall height of the tibial keel 14.

The projections 20, 22 are shown to be of a particular construction. For instance, projection 20 is a long, thin rectangular structure that plateaus in a solid edge 32 (discussed more fully below). Likewise, projection 22 includes a solid edge 32, but is somewhat shorter and thinner than projection 20. It is contemplated that the projections 20, 22 can encompass other shapes, including but not limited to, curved bodies or the like. Moreover, it is contemplated that the projections could comprise a plurality of components. For example, projection 20 could encompass a plurality of more square shaped components that are placed adjacent to each other or spaced apart a distance. Solid edge 32 could also be replaced with a sharper or narrower surface than the substantially flat surface that is depicted. Still further, it is to be understood that although shown of a particular design, extensions 26 and fins 34 can encompass many different types of designs. For one, both projections could include either extensions 26, fins 34 or a combination thereof. Additionally, the extensions 26 and fins 34 could be of different shapes and sizes. By way of example, it is contemplated for either or both of projections 20, 22 to include a plurality of teeth or spikes in lieu of the depicted extensions 26 and fins 34.

Figure 19:
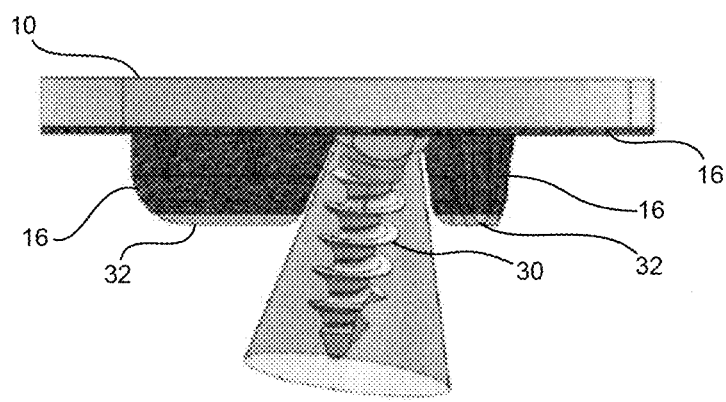
FIG. 19 is a side view of the unicondylar tibial implant of FIGS. 9-18 with a bone screw positioned within a through hole of the tibial implant.
Figure 20:
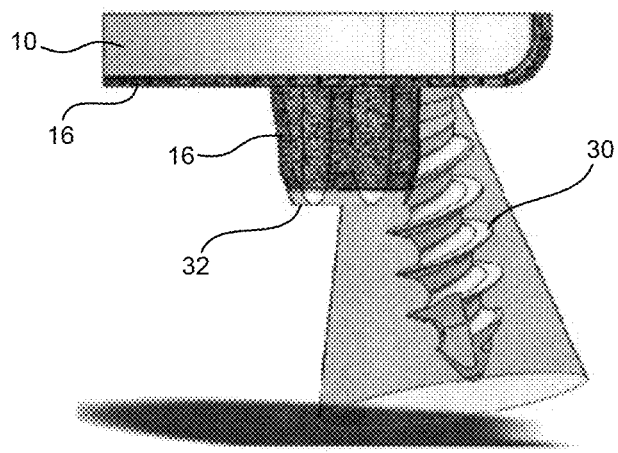
FIG. 20 is a rear view of the assembly of FIG. 19.
Figure 21:
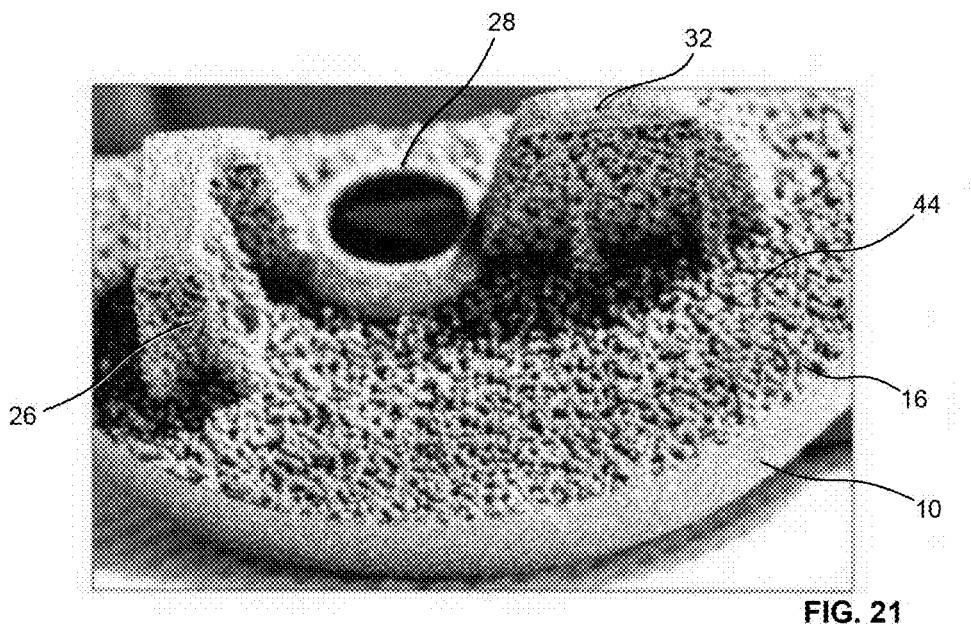
Figure 22:
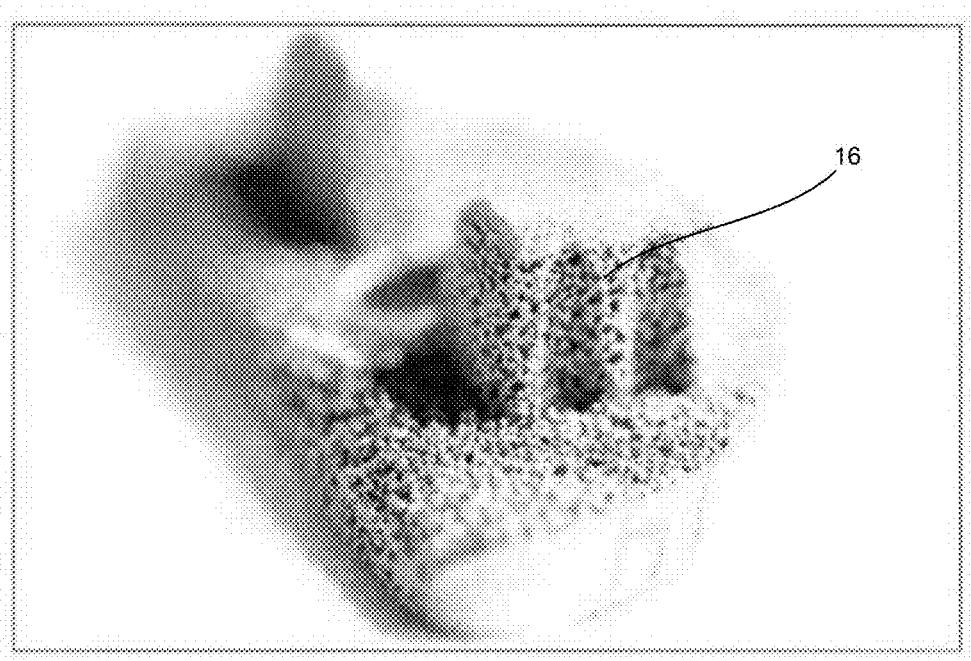
Figure 23:
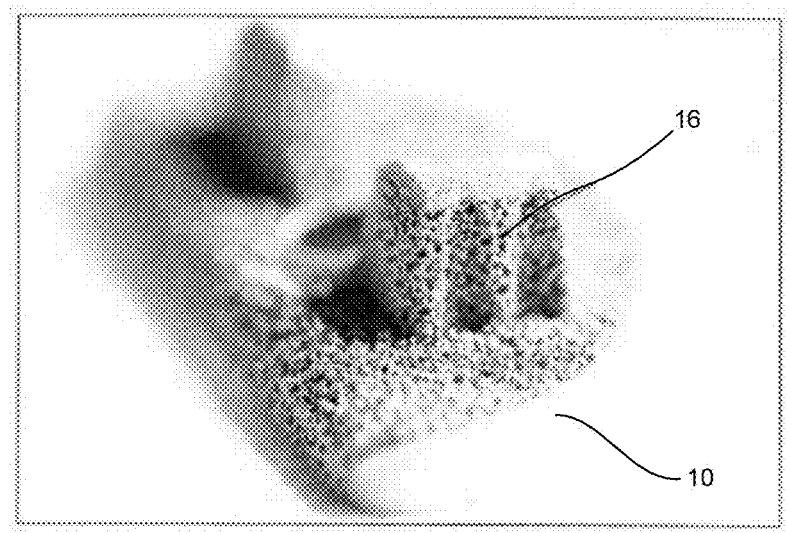
Figure 24:
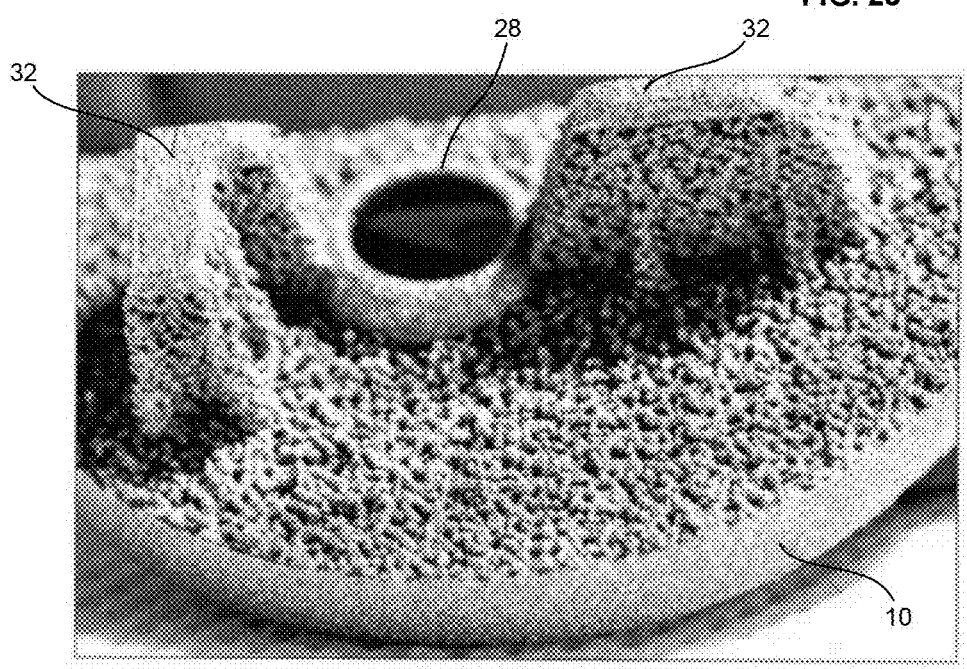
Figure 27:
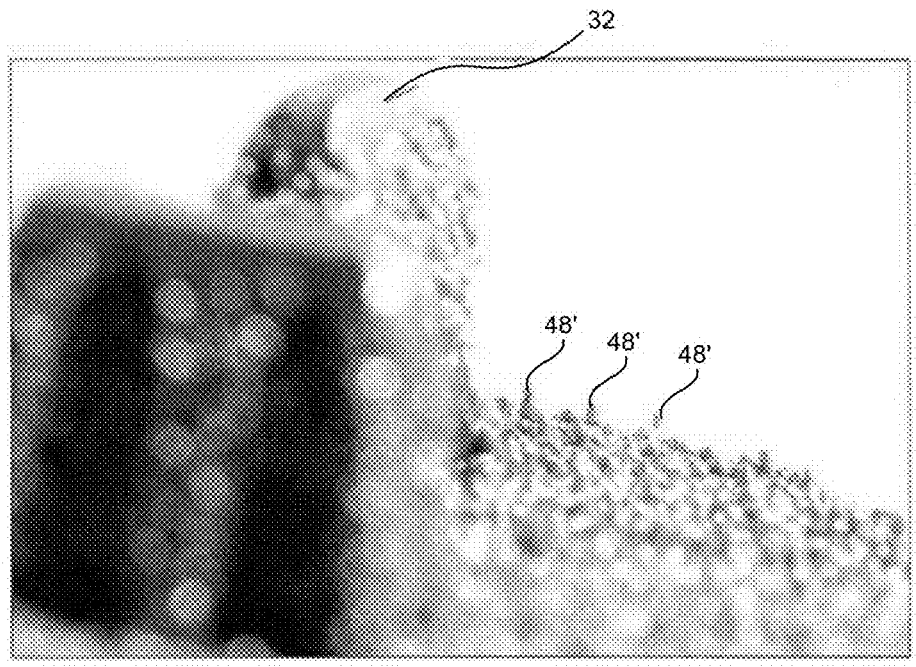
Figure 28:
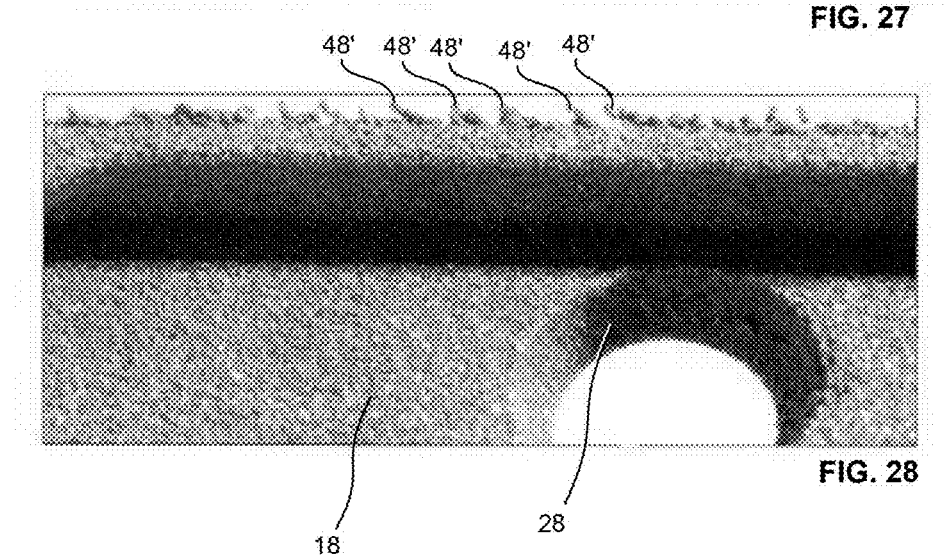
Figure 29:
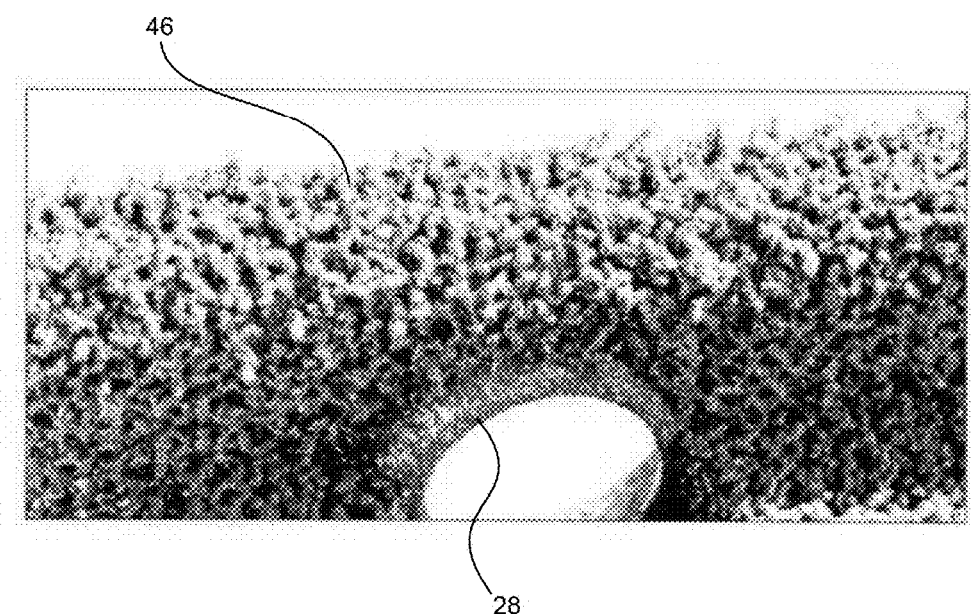

The tibial implant 10 can optionally be configured with a through hole or aperture 28 (best shown in FIGS. 2, 5 and 21) through which another device, instrument or material e.g., a bone screw 30 (as is shown in FIGS. 19 and 20) can be inserted therethrough. The through hole 28 is shown splitting the keel 14 into projections 20, 22 and may pass through one or more of the projections 20, 22 thereby interrupting their general shape. For instance, as can be seen in FIG. 5, material is removed from projections 20, 22 around or adjacent the through hole 28 to provide for clearance of the device (bone screw 30 or the like), instrument or material to be inserted therethrough.

Preferably, the through hole 28 is shaped and sized for the passage of the bone screw 30 (best shown in FIGS. 19 and 20) through a superior aspect of the tibial implant 10 into the bone beneath the underside or inferior surface of the tibial tray 10. The through hole 28 is preferably designed so that the bone screw 30 can be angulated to achieve a desired direction by the user. Further, with material from adjacent projection 20 removed, the projection 20 does not interfere with the passage of the bone screw 30 through the through hole 28. Such bone screws 30 are readily known in the art and a detailed description of their structure and operation is not necessary for a complete understanding of the present invention.

The tibial implant 10 may employ the use of a knockout plug 36 formed within the through hole 28 and out of a material that is metallurgically continuous with the greater bulk of the tibial implant 10. The knockout plug 36 is configured to be removed from the remainder of the tibial implant 10 via a boundary shear section or weakened area 38 around the plug 36 (see FIG. 5) upon the application of a suitable force. The plug 36 may be machined into the tibial tray 10 or built in final form through an additive manufacturing process such as by direct metal laser sintering (discussed more fully below). Preferably, the through hole 28, is obstructed by the knockout plug 36 so that the superior surface 40 of the tibial tray 10 facing the bearing component 12 is fully continuous without any path through which debris or material could pass through the tibial tray 10 to the bone engaging underside of the tibial implant 10. Thus, in the event of backside wear of the bearing component 12, wear particles are less likely to migrate out of the tibial tray 10 than if an already present through hole were in place. The knockout plug 36 can optionally include a threaded stud 42 (best shown in FIG. 12), which mates to instrumentation to facilitate removal of the knockout plug 36.

In sum, the tibial tray 10 has an initially covered through hole 28 into which a screw 30 can be placed to further stabilize the tibial implant 10 to the prepared bone upon implantation. This is especially advantageous for initial implant stability and when placing the tibial implant into bone of questionable density where the user/surgeon is not confident the bone itself is stable enough to support adequate short term stability.

The general shape of the tibial keel 14 is designed to maximize surface area to volume ratio for the tibial keel 14 to enhance bone ingrowth thereto (discussed more below) while minimizing the amount of bone removal during bone preparation. The amount of surface area available for bone ingrowth is important for both short and long term fixation of the implant to the bone. Short term fixation is also achieved by "press-fitting" the larger body of the keel into a smaller preparation of the bone. Once in place, the residual stresses from the compressed bone around the tibial keel 14 increase the frictional forces against the tibial keel 14 and increase the stability of the tibial implant 10 into the prepared bone. Increasing the surface area over which the press-fit interference is effective helps to increase the total frictional forces available to contribute to stability of the implant and to distribute frictional forces over a greater effective area of the tibial implant 10.

Long term fixation of the tibial implant 10 is enhanced by the areas of the tibial implant 10 having the porous structure and surface, hereafter referred to as 'porous metal' (generally referred to with reference numeral 16). As the bone remodels and grows into the porous metal 16, the frictional retention forces will be replaced and/or supplemented with bone ingrowth. The degree of this fixation via bone ingrowth is, in part, a function of the amount and distribution of the porous metal surface area available for ingrowth. The large distributed tibial keel surface area thereby provides a structure for increased stability via a larger area of bone ingrowth.

The porous metal 16 is formed from a porous structured biomaterial, and includes a plurality of struts 44 (best shown in FIGS. 21-29) having varying lengths and cross sections. At least one strut of the porous metal 16 has an end connected to one or more other struts at node points 46 (see FIG. 29) thereby forming the porous geometry of the porous metal 16. The porous metal 16 also includes boundary struts 48 (see FIGS. 26, 27 and 28) that are configured to extend beyond a nominal boundary of the porous metal 16. That is, the porous metal 16 has boundary struts 48 that extend away from the surface of the porous metal 16 in a finger-like or hair follicle-like fashion. The extending boundary struts 48 impart a roughness to the surface, the degree of which is dependent upon the number and length of boundary struts 48 present. The average or main direction of the boundary struts 48 also impart a surface roughness that varies dependent upon which direction the device is driven for implantation.

Preferably, the tibial keel 14 is formed from a metal substrate and a layer of porous metal 16 adjacent the substrate. The porous metal 16 on the tibial keel 14 includes extending boundary struts 48 with unconnected ends pointing or extending towards the bottom or inferior surface of the tibial tray 10. Under similar loading conditions, sliding over the angled struts toward the bottom surface of the tibial tray 10 will experience less frictional forces than bone sliding away from the bottom face of the tibial tray 10. Preferably, the boundary struts 48 are angled about +/−10 degrees from normal to a surface of the substrate to which the porous metal 16 is applied to.

Another element of the present invention is that the boundary struts 48 are oriented in a predetermined direction such that they push or are directed towards the bone interface surface. While the surface of the porous metal 16 may exhibit characteristics of a rougher surface, the boundary struts 48 of the porous metal 16 implanted into a bone interface embed themselves into the bone and provide a mechanical interlock to the surrounding bone. This is especially advantageous during initial implantation for initial fixation purposes. In the aggregate, the plurality of boundary struts 48 significantly improves the overall stability of the tibial implant 10 upon initial implantation. Preferably, the bottom surface of the tibial tray 10 has extending boundary struts 48' (best shown in FIGS. 26 and 27) in a direction substantially normal to the bottom surface of the tibial tray 10. As the tibial implant 10 is definitively seated against the bone interface surface, the boundary struts 48' pierce the surface of the prepared bone to increase stability of the tibial implant 10 to the bone.

In the disclosed embodiment, the tibial implant 10 has the porous metal 16 on all surfaces that make contact with bone. The surface of the porous metal 16 is tailored for each specific region of the tibial implant 10 to have specific surface roughness and thereby specific amounts of friction when engaged with bone. That is, the tibial implant 10 is configured to have a porous metal 16 with boundary struts 48 at predetermined angles dependent upon the location of the porous metal 16 on the tibial implant 10.

In sum, the surfaces of the porous metal 16 have extending boundary struts 48 which serve to modify the surface roughness of the tibial implant 10. The size and average direction of the extending boundary struts 48 impart different frictional coefficients depending upon the direction the boundary struts 48 extend. The boundary struts 48 can also be directed in a direction largely normal to the surface from which they extend from. This can have an additive anchoring effect which enhances stability of the tibial implant 10 to the bone.

A solid edge 32 (best shown in FIGS. 2, 7 and 21) at the distal end of one or both of the projections 20, 22 of the tibial keel 14 prevents bone from growing into the tibial keel 14 from the bottom up. Thus, while the majority of the surface area of the tibial implant 10 is design for fixing (via bone ingrowth), no such fixing occurs at the distal ends of the projections. Rather, the fixing of the tibial implant 10 to the bone occurs only at the perimeter of the tibial keel 14, i.e., the lateral side surfaces of the tibial keel 14. That is, the tibial implant 10 is configured to prevent any bone ingrowth or fixation about a distal surface of the tibial keel 14 via the solid edge 32. Preventing bone ingrowth about the distal surface of the tibial keel 14 allows for easier removal of the implant (e.g., during a revision procedure), if necessary, since bone ingrowth on such distal surfaces of the tibial keel 14 represents areas that are most problematic to achieving separation of the implant from bone during revision procedures. In other words, as an implant is pulled out of bone, bony ingrowth into the bottom portion of the tibial keel might not separate from the greater volume of the bone exactly at the implant interface but rather somewhere deeper within the volume of bone beneath the implant. If this occurs during implant removal, the additional bone that would otherwise be inadvertently removed would complicate the revision procedure and drive the use of more significant revision components. In any event, the bone which engages and contacts the bottom of the tibial keel 14 represents a small fraction of the overall surface area of the tibial implant 10.

The porous metal 16 of implant 10 may be formed utilizing any suitable process. For instance, a selective laser melting or sintering process may be employed to create the porous metal 16, or even the entirety of the implant 10. In conjunction with the latter, it is contemplated that the implant 10 may include substantially non-porous or solid portions and the porous metal 16 portions that are formed from the same process. Examples of such processes are disclosed in U.S. Pat. No. 7,537,664, and U.S. Patent Application Publication Nos. 2006/0147332 and 2007/0142914, the disclosures of each or incorporated by reference herein. Of course, it is contemplated to utilize any known and suitable process to form implant 10.

Figure 32:
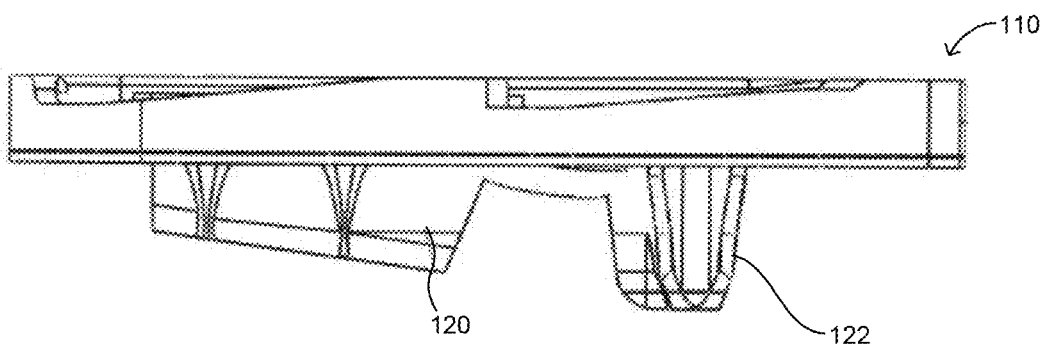
FIG. 32 is a side view of the unicondylar tibial implant of FIG. 30.
Figure 33:
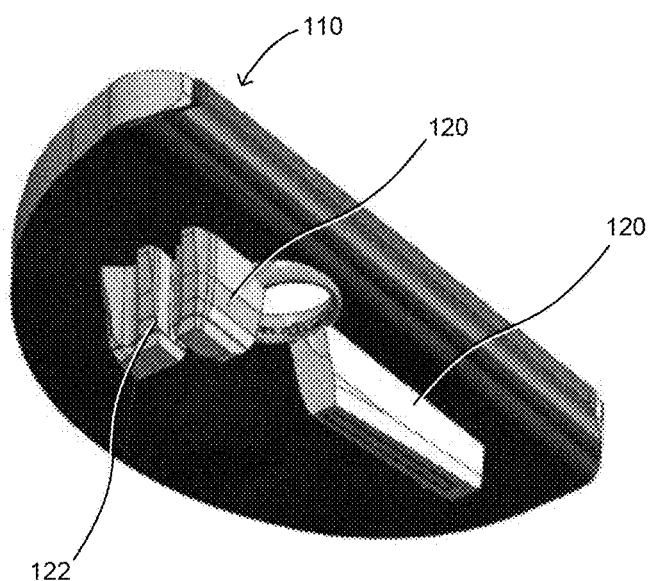
FIG. 33 is a bottom perspective view of the unicondylar tibial implant of FIG. 30.

Referring to FIGS. 30-33, in accordance with another preferred embodiment, the present invention provides for a tibial implant 110. The tibial implant 110 is similarly configured as tibial implant 10, except as noted below. For instance, while the tibial implant 10 includes first and second projections 120, 122 that are similarly configured to projections 20, 22, projection 120 is sloped (see FIG. 32) and is segmented into two different portions by the void created by hole 128 (see FIG. 33). Moreover, the second projection 122 does not take up as much surface area as does second projection 22. As best shown in FIG. 32, the height of the first projection 120 slopes towards the posterior end of the tibial implant 110 such that the height of the first protrusion decreases as it extends from the anterior end towards the posterior end. Of course, projection 120 could slope in any direction.

Figure 34:
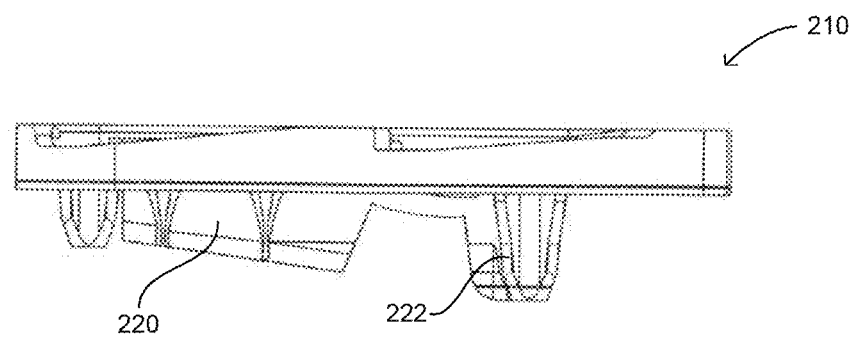
FIG. 34 is a side view of a unicondylar tibial implant in accordance with yet another embodiment of the present invention.
Figure 35:
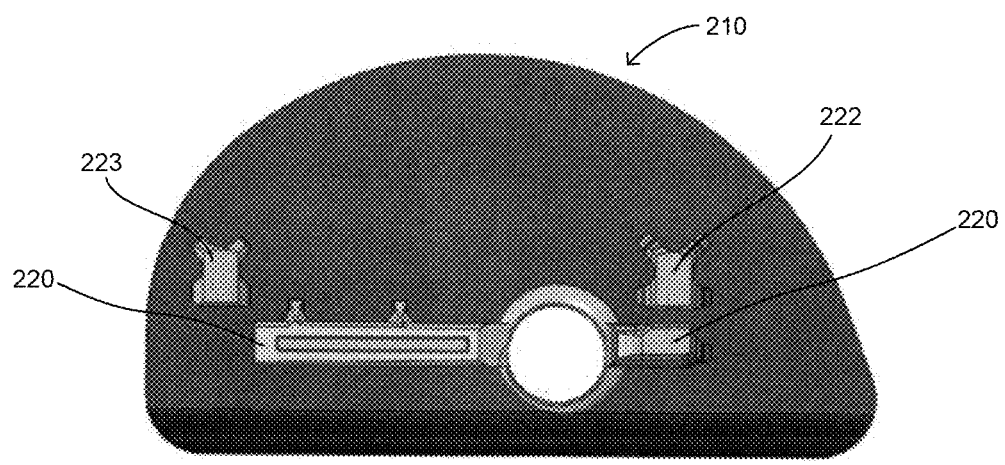
FIG. 35 is a bottom view of the unicondylar tibial implant of FIG. 34.

Referring to FIGS. 34 and 35, in accordance with yet another preferred embodiment, the present invention provides for a tibial implant 210. The tibial implant 210 is similarly configured as tibial implant 110, except as noted below. In particular, implant 210 includes a third protrusion 223, which like the second protrusion 222, is slightly spaced apart from the first protrusion 220 and may include extensions. Preferably, the third protrusion 223 is positioned more towards the rear or posterior to the first protrusion and has a height similar to the height of the posterior end of the first protrusion 220 to which it is adjacent to. However, the height of the third protrusion 223 is less than that of the second protrusion 222. The longitudinal axis of the third protrusion 223 is also configured not to intersect the longitudinal axis of the first protrusion 220.

Figure 36:
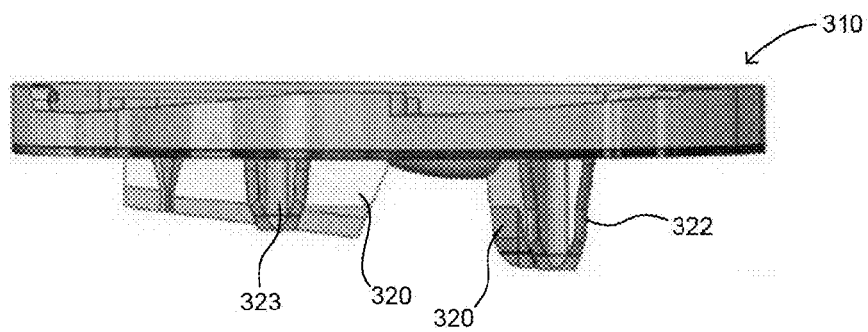
FIG. 36 is a side view of a unicondylar tibial implant in accordance with a further embodiment of the present invention.
Figure 37:
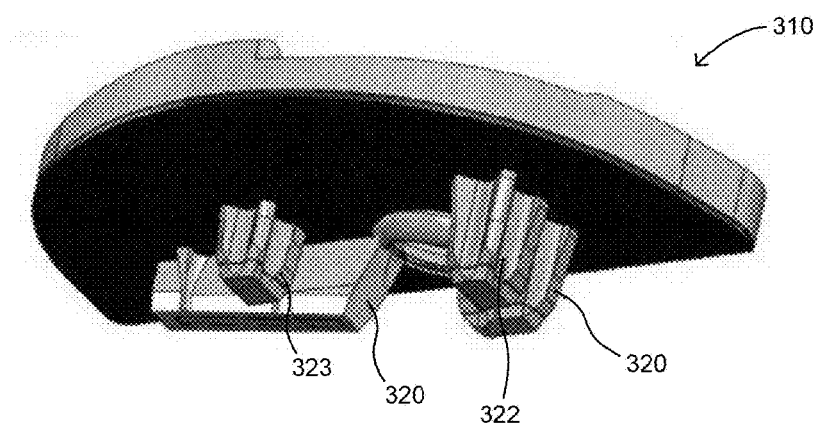
FIG. 37 is a bottom perspective view of the unicondylar tibial implant of FIG. 36.
Figure 38:
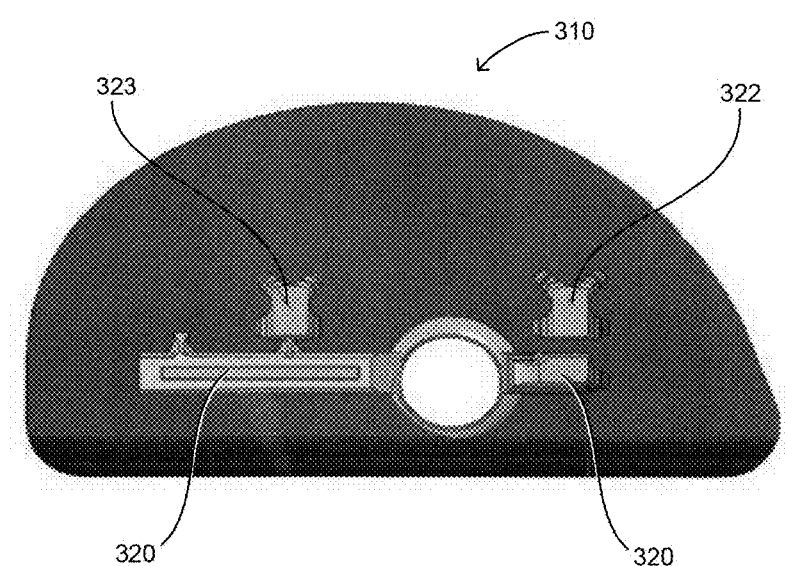
FIG. 38 is a bottom view of the unicondylar tibial implant of FIG. 36.

FIGS. 36-38 depict yet another embodiment implant 310, which is similar to the implant 210 save for the placement of the third protrusion 323 more toward or about a middle section of the first protrusion 320. When positioned about the middle section of the first protrusion 320, the third protrusion 323 has a height substantially the same as the area of the first protrusion 320 that it is adjacent to.

Figure 39:
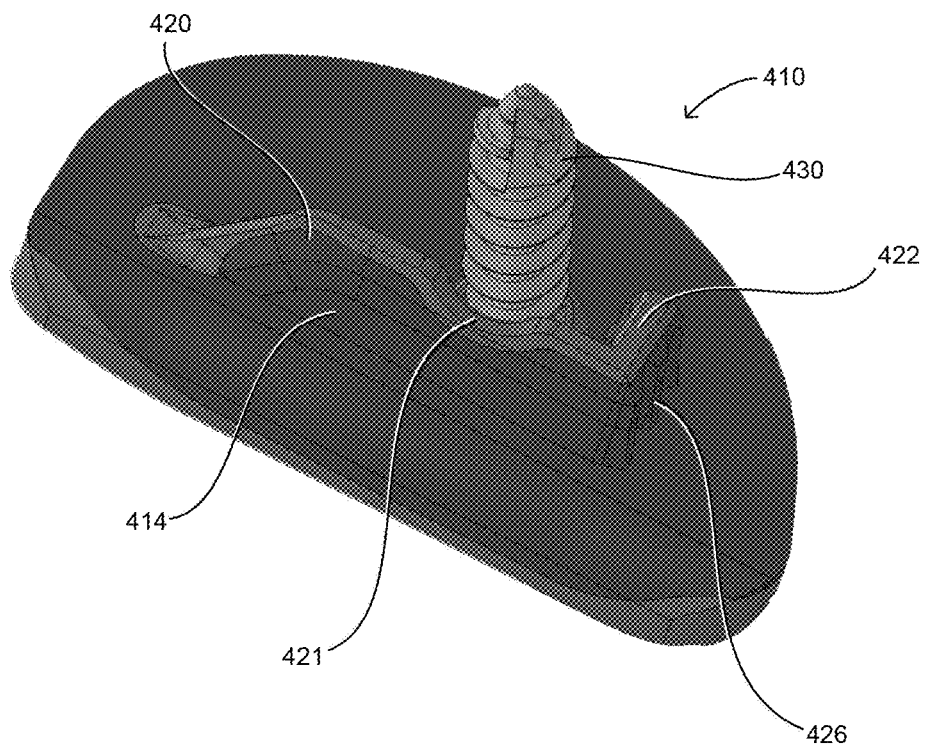
FIG. 39 is a bottom perspective view of a unicondylar tibial implant according to another embodiment of the present invention.
Figure 40:
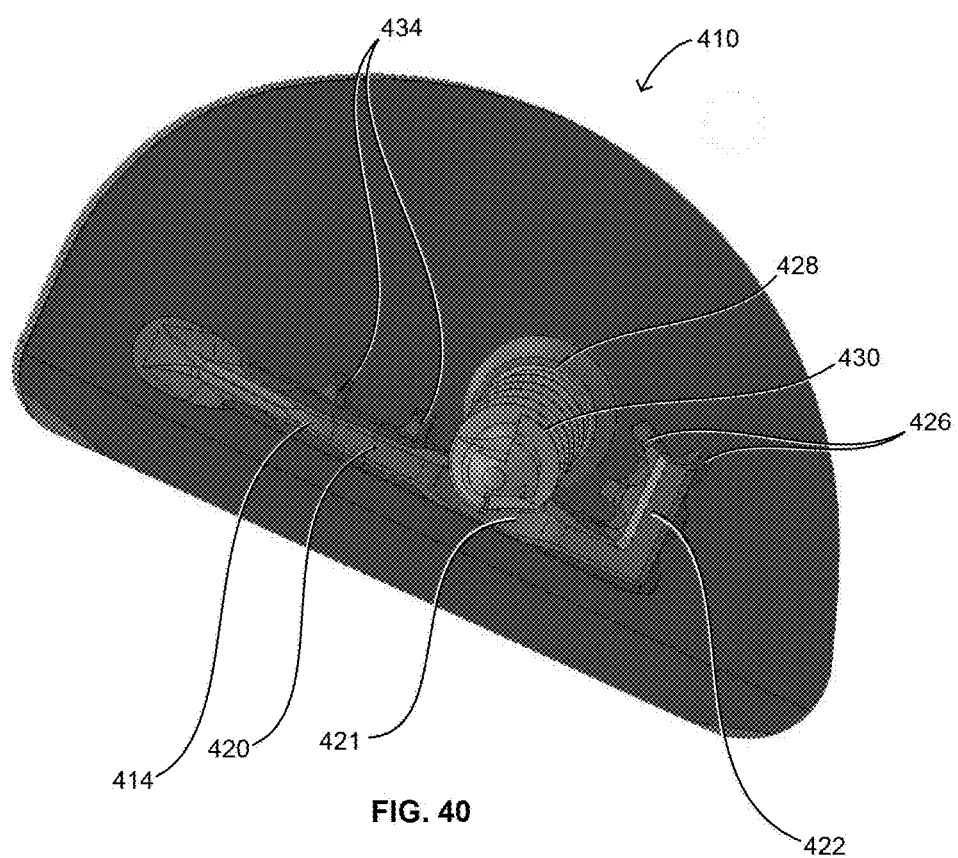
FIG. 40 is another bottom perspective view of the unicondylar tibial implant of FIG. 39.

FIGS. 39 and 40 depict yet another embodiment tibial implant 410. Unlike the above-discussed implants, implant 410 includes a keel 414 that is of a unitary design. A hole or aperture 428 is situated offset with respect to the keel 414. This allows for the keel 414 to have a unitary construction (i.e., it is not broken up by the hole 428 as in the above designs). Like the foregoing embodiments, keel 414 includes two projections 420, 422, with the projection 420 including fins 434 and the projection 422 including extensions 426. Of course, as in the above embodiments, either projection could include either or both of the extensions 426 or fins 434, and such structures can be of any shape and or size with respect to the projections. Moreover, keel 414 includes a rounded cut out 421, which allows for a screw 430 to angulate with respect to implant 410. In other words, the cut out 421 provides clearance for the screw 430 to move with respect to the plate in directions towards the keel 414.

It will be appreciated by those skilled in the art that changes could be made to the embodiments described above without departing from the broad inventive concept thereof. For example, additional components can be added to the tibial implant assembly. It is to be understood, therefore, that this invention is not limited to the particular embodiments disclosed, but it is intended to cover modifications within the spirit and scope of the present invention as described above.

It is also to be understood that the disclosure set forth herein includes all possible combinations of the particular features described. For example, where a particular feature is disclosed in the context of a particular aspect, arrangement, configuration, or embodiment, or a particular claim, that feature can also be used, to the extent possible, in combination with and/or in the context of other particular aspects, arrangements, configurations, and embodiments of the invention, and in the invention generally.

Furthermore, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic implant for replacing a portion of a bone comprising:
    a bone contacting surface;
    a hole configured to accept a bone screw at a plurality of different angles;
    a keel extending from the bone contacting surface, the keel including a first projection with a first longitudinal axis and a second projection with a second longitudinal axis, wherein the first and second longitudinal axes are oriented orthogonally to each other and separated from each other by the hole and at least one of the first and second projections includes a sloped surface; and
    a porous portion adapted to allow for the bone to grow therein, the porous portion defining a first porous surface and at least one bonding strut extending 0 to 10° from normal to the first porous surface.

2. The orthopedic implant of claim 1, wherein the hole includes a plug removable upon the application of a force.

3. The orthopedic implant of claim 1, further comprising at least one fin associated with the first projection and extending oblique to the first longitudinal axis.

4. The orthopedic implant of claim 3, wherein the fin is shaped to engage the bone.

5. The orthopedic implant of claim 4, wherein the fin is configured to enter into an unprepared portion of the bone.

6. The orthopedic implant of claim 1, further comprising at least one extension associated with the second projection and extending oblique to the second longitudinal axis.

7. The orthopedic implant of claim 6, wherein the at least one extension is shaped to engage the bone.

8. The orthopedic implant of claim 7, wherein the at least one extension frictionally engages the bone.

9. The orthopedic implant of claim 1, wherein the porous portion covers at least a portion of the bone contacting surface and at least a portion of the keel.

10. The orthopedic implant of claim 9, further comprising a solid portion at a distal end of the keel.

11. The orthopedic implant of claim 1, further comprising a third projection.

12. The orthopedic implant of claim 1, further comprising a bearing component attachable to the implant.

13. The orthopedic implant of claim 1, wherein the implant is a unicondylar tibial baseplate.

14. A kit comprising the implant of claim 1 and at least one other implant.

15. A tibial baseplate comprising:
    a bone contacting surface having anterior, posterior, medial and lateral sides;
    a first projection extending from the bone contacting surface and having a first length extending in a first direction between the anterior and posterior ends;
    a second projection extending from the bone contacting surface and having a second length extending in a second direction between the medial and lateral sides, at least one of the first and second projections including a sloped surface;
    an aperture for receiving a bone screw, the first and second projections separated by the aperture; and
    a porous material for promoting bone ingrowth, the porous material at least partially covering the bone contacting surface, the first projection and the second projection.

16. The tibial baseplate of claim 15, further comprising a third projection.

17. The tibial baseplate of claim 15, wherein the porous material defines a plurality of boundary struts extending from the bone contacting surface in a first direction.

18. The tibial baseplate of claim 17, wherein the boundary strut extends from 0 to 10 degrees from normal to the bone contacting surface.

19. The tibial baseplate of claim 15, wherein the aperture is configured to accept a bone screw at a plurality of different angles.

20. The tibial baseplate of claim 15, wherein the aperture includes a plug removable upon the application of a force.

21. The tibial baseplate of claim 15, further comprising at least one fin or extension associated with at least one of the first and second projections.

22. The tibial baseplate of claim 21, wherein the fin is configured to enter into an unprepared portion of the bone and the extension frictionally engages the bone.

23. The tibial baseplate of claim 15, further comprising a solid portion at distal ends of the first and second projections.

24. A tibial baseplate comprising:
- a bone contacting surface having anterior, posterior, medial and lateral sides;
- a first projection extending from the bone contacting surface and having a first length extending in a first direction between the anterior and posterior ends;
- a second projection extending from the bone contacting surface and having a second length extending in a second direction between the medial and lateral sides, at least one of the first and second projections including a sloped surface;
- an aperture for receiving a bone screw, the aperture separating the first and second projections;
- a plug at least partially covering the aperture, the plug being removable upon the application of a force; and
- a porous material for promoting bone ingrowth, the porous material at least partially covering the bone contacting surface, the first projection and the second projection, wherein the porous material defines a plurality of boundary struts extending from the bone contacting surface from 0 to 10 degrees from normal to the bone contacting surface.

* * * * *